United States Patent
Wittekind et al.

(10) Patent No.: US 11,357,833 B2
(45) Date of Patent: *Jun. 14, 2022

(54) USE OF LYSIN TO RESTORE/AUGMENT ANTIBACTERIAL ACTIVITY IN THE PRESENCE OF PULMONARY SURFACTANT OF ANTIBIOTICS INHIBITED THEREBY

(71) Applicant: ContraFect Corporation, Yonkers, NY (US)

(72) Inventors: Michael Wittekind, Bainbridge Island, WA (US); Raymond Schuch, Mountain Lakes, NJ (US)

(73) Assignee: CONTRAFECT CORPORATION, Yonkers, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/760,416

(22) PCT Filed: Sep. 16, 2016

(86) PCT No.: PCT/US2016/052348
§ 371 (c)(1),
(2) Date: Mar. 15, 2018

(87) PCT Pub. No.: WO2017/049242
PCT Pub. Date: Mar. 23, 2017

(65) Prior Publication Data
US 2019/0290672 A1 Sep. 26, 2019

Related U.S. Application Data

(60) Provisional application No. 62/220,212, filed on Sep. 17, 2015, provisional application No. 62/247,619, filed on Oct. 28, 2015.

(51) Int. Cl.
| | | |
|---|---|---|
| *A61K 38/47* | (2006.01) |
| *A61K 38/12* | (2006.01) |
| *A61K 45/06* | (2006.01) |
| *A61K 9/00* | (2006.01) |
| *A61K 31/7036* | (2006.01) |
| *A61K 38/46* | (2006.01) |
| *A61K 38/16* | (2006.01) |
| *A61P 31/04* | (2006.01) |
| *C12N 9/36* | (2006.01) |

(52) U.S. Cl.
CPC ............ *A61K 38/47* (2013.01); *A61K 9/0019* (2013.01); *A61K 9/0073* (2013.01); *A61K 31/7036* (2013.01); *A61K 38/12* (2013.01); *A61K 38/162* (2013.01); *A61K 38/46* (2013.01); *A61K 45/06* (2013.01); *A61P 31/04* (2018.01); *C12N 9/2462* (2013.01); *C12Y 302/01017* (2013.01); *A61K 2121/00* (2013.01); *Y02A 50/30* (2018.01)

(58) Field of Classification Search
CPC ........... C12N 9/2462; C12Y 302/01017; A61P 31/04; A61K 9/0019; A61K 9/0073; A61K 31/7036; A61K 38/12; A61K 38/162; A61K 38/46; A61K 45/06; A61K 2121/00; A61K 38/16

See application file for complete search history.

(56) References Cited

U.S. PATENT DOCUMENTS

| | | |
|---|---|---|
| 8,846,865 B2 | 9/2014 | Briers et al. |
| 9,034,322 B2 | 5/2015 | Fischetti et al. |
| 2013/0302306 A1 | 11/2013 | Schuch et al. |
| 2014/0094401 A1 | 4/2014 | Farris |
| 2014/0120074 A1 | 5/2014 | Miller |
| 2015/0118731 A1 | 4/2015 | Lavigne et al. |
| 2020/0376096 A1* | 12/2020 | Schuch ............... A61K 9/0019 |

FOREIGN PATENT DOCUMENTS

| | | |
|---|---|---|
| JP | 2010534684 A | 11/2010 |
| WO | 2012/085259 | 6/2012 |
| WO | WO2013170015 | 11/2013 |
| WO | 2014124047 A1 | 8/2014 |
| WO | 2015/070911 | 5/2015 |
| WO | 2015/070912 | 5/2015 |
| WO | 2015/071436 | 5/2015 |
| WO | 2015/071437 | 5/2015 |

OTHER PUBLICATIONS

Lood et al. Novel Phage Lysin Capable of Killing the Multidrug-Resistant Gram Negative Bacterium Acinetobacter baumannii in a Mouse Bacteremia Model. Antimicrobial Agents and Chemotherapy (2015), 59(4): 1983-1991, Epub Jan. 20, 2015.*
Herrmann et al. Colistin-Tobramycin Combinations Are Superior to Monotherapy Concerning the Killing of Biofilm Pseudomonas aeruginosa. JID 2010:202: 1585-1592.*
Briers et al. Art-175 Is a Highly Efficient Antibacterial against Multidrug-Resistant Strains and Persisters of Pseudomonas aeruginosaAntimicrobial Agents and Chemotherapy p. 3774-3784 Jul. 2014 vol. 58 No. 7.*
Uchiyama, Jumpei, et al., "Characteristics of a novel Pseudomonas aeruginosa bacteriophage, PAJU2, which is genetically related to bacteriophage D3", Virus Research, 2009, 139, pp. 131-134.

(Continued)

*Primary Examiner* — Iqbal H Chowdhury
(74) *Attorney, Agent, or Firm* — MH2 Technology Law Group LLP

(57) ABSTRACT

The present disclosure relates to methods for restoring or augmenting bactericidal activity of an antibiotic in an organ or tissue in which pulmonary surfactant is present. More specifically, the present disclosure describes that inhibition of antibiotics due to environmental factors, such as the presence of pulmonary surfactant in an organ or tissue such as the respiratory epithelium can be sidestepped or overcome and the effectiveness of the antibiotic in that milieu restored or augmented by co-administration of an antibiotic and a lysin.

17 Claims, 5 Drawing Sheets

Specification includes a Sequence Listing.

(56) References Cited

OTHER PUBLICATIONS

Anonymous: "putative endolysin [Pseudomonas phage PAJU2]", NCBI, Feb. 18, 2009, Retrieved from the Internet: https://www.ncbi.nim.nih.gov/protein/YP_002284361.1, abstract.
International Search Report for PCT/US2016/052348 dated Mar. 28, 2017.
Nguyen, Klen T., et al., "Genetically engineered lipopeptide antibiotics related to A54145 and daptomycin with improved properties", Antimicrob. Agents Chemother., 2010, 54(4), pp. 1404.
Schuch, Raymond, et al., "Combination therapy with lysin CF-301 and antibiotic is superior to antibiotic alone for treating methicillin-resistant *Staphylococcus aureus*-induced murine bacteremia", The Journal of Infectious Diseases, , 2014, 209, pp. 1469-1478.
Schwameis, R., et al., "Effect of pulmonary surfactant on antimicrobial activity In Vitro", Antimicrobial Agents and Chemotherapy, Oct. 2013, vol. 57, No. 10, pp. 5151-5154.
Silverman, Jared A., et al., "Inhibition of daptomycin by pulmonary surfactant: In Vitro modeling and clinical impact", The Jouranl of Infectious Diseases, 2005, 191, pp. 2149-2152.
Van't Veen, Annemarie, et al., "Influence of pulmonary surfactant on In Vitro bactericidal activities of amoxicillin, ceftazidime, and tobramycin", Antimicrobial Agents and Chemotherapy, Feb. 1995, pp. 329-333.
Vouillamoz, Jacques, et al., "Bactericidal synergism between daptomycin and the phage lysin Cpl-1 in a mouse model of pneumococcal bacteraemia", International Journal of Antimicrobial Agents, 2013, 42, pp. 416-421.
Wittekind, Michael, et al., "Cell wall hydrolases and antibiotics: exploiting synergy to create efficactious new antimicrobial treatments", Current Opinion in Microbiology, 2016, 33, pp. 18-24.
English-language translation of Israeli Office Action issued in Israeli Patent Application No. 258123 dated Feb. 27, 2019, pp. 1-3.
Becker, S.C. et al., The phage K lytic enzyme LysK and lysostaphin act synergistically to kill MRSA, FEMS Microbiol. Lett. 2008; 287:185-191.
Cheng, Q. et al., Removal of Group B Streptococci Colonizing the Vagina and Oropharynx of Mice with a Bacteriophage Lytic Enzyme, Antimicrob. Agents Chemother. 2005; 49(1):111-117.
Fenton, M. et al., Recombinant bacteriophage lysins as antibacterials, Bioengineered Bugs 2010; 1(1):9-16.
Garcia, J.L. et al., Cloning, Purification, and Biochemical Characterization of the Pneumococcal Bacteriophage Cp-1 Lysin, J. Virol. 1987; 61(8):2573-2580.
GenBank Database: AB254389.1, Oct. 5, 2006, available at https://www.ncbi.nlm nih.gov/nuccore/ab254389.1, pp. 1-4.
GenBank AFN38929.1, Mar. 28, 2014, available at https://www.ncbi.nlm.nih.gov/protein/AFN38929.1, pp. 1-3.
GenBank KJ740396.1, Apr. 1, 2005, available at https://www.ncbi.nlm.nih.gov/nuccore/kj740396.1, pp. 1-2.
Gilmer, D.B. et al., Novel Bacteriophage Lysin with Broad Lytic Activity Protects against Mixed Infection by *Streptococcus pyogenes* and Methicillin-Resistant *Staphylococcus aureus*, Antimicrob. Agents Chemother. 2013; 57(6):2743-2750.
Goerke, J., Pulmonary surfactant: functions and molecular composition, Biochim et Biophys. Acta 1998; 1408:79-89.
Jung, D. et al., Structural Transitions as Determinants of the Action of the Calcium-Dependent Antibiotic Daptomycin, Chem. Biol. 2004; 11:949-957.
Lakey, J.H. et al., Fluorescence Indicates a Calcium-Dependent Interaction between the Lipopeptide Antibiotic LY146032 and Phospholipid Membranes, Biochemistry 1988; 27:4639-4645.
Lood, R. et al., A Highly Active and Negatively Charged *Streptococcus pyogenes* Lysin with a Rare D-Alanyl-L-Alanine Endopeptidase Activity Protects Mice against Streptococcal Bacteremia, Antimicrob. Agents Chemother. 2014; 58(6):3073-3084.
Madsen, J. et al., Expression and Localization of Lung Surfactant Protein A in Human Tissues, Am. J. Respir. Cell Mol. Biol 2003; 29(5):591-597.

Martin, A.C. et al., Nucleotide Sequence and Transcription of the Left Early Region of *Streptococcus pneumoniae* Bacteriophage Cp-1 Coding for the Terminal Protein and the DNA Polymerase, Virology 1995; 221:21-32.
McGowan, S. et al., X-ray crystal structure of the streptococcal specific phage lysin PlyC, Proc. Natl. Acad. Sci. USA 2012; 109(31):12752-12757.
Nelson, D. et al., PlyC: A multimeric bacteriophage lysin, Proc. Natl. Acad. Sci. USA 2006; 103(28):10765-10770.
Nguyen, K.T. et al., Genetically Engineered Lipopeptide Antibiotics Related to A54145 and Daptomycin with Improved Properties, Antimicrob. Agents Chemother. 2010; 54(4):1404-1413.
Oeschlin, F. et al., In Vitro Characterization of PlySK1249, a Novel Phage Lysin, and Assessment of Its Antibacterial Activity in a Mouse Model of *Streptococcus agalactiae* Bacteremia, Antimicrob. Agents Chemother. 2013; 57(12):6276-623.
Pritchard, D.G. et al., LamdaSa1 and LambdaSa2 Prophage Lysins of *Streptococcus agalactiae*, Appl. Environmental Microbiol. 2007; 73(22):7150-7154.
English-language translation of Russian Office Action issued in corresponding Russian Patent Application No. 2018107249/04 dated Jan. 10, 2020, pp. 1-8.
Varea, J. et al., Structural and Thermodynamic Characterization of Pal, a Phage Natural Chimeric Lysin Active against Pneumococci, J. Biol. Chem. 2004; 279(42):43697-43707.
Yang, H. et al., Novel Chimeric Lysin with High-Level Antimicrobial Activity against Methicillin-Resistant *Staphylococcus aureus* In Vitro and In Vivo, Antimicrob. Agents Chemother. 2014; 58(1):536-542.
Office Action issued in Israeli Patent Application No. 258123 dated Jul. 30, 2020 with English language translation (5 pages).
Office Action issued in Japanese Patent Application No. 2018-513834 dated Sep. 15, 2020 with English language translation (14 pages).
Briers et al., Engineered Endolysin-Basin Artilysins to Combat Multidrug-Resistant Gram-Negative Pathogens, MBio. 2014; 4:e01379-14.
Brogden N. et al, Will new generations of modified antimicrobial peptides improve their potential as pharmaceuticals, Int J Antimicrob Agents. 2011; 38(3): 217-225.
Deslouches, B. et al, Activity of the De Novo Engineered Antimicrobial Peptide WLBU2 against Pseudomonas aeruginosa in Human Serum and Whole Blood: Implications for Systemic Applications, Antimicrobial Agents Chemotherapy 2005; 49(8):3208-3216.
Fischetti, V., Bacteriophage lysins as effective antibacterials, Curr Opin Microbiol. 2008; 11(5): 393-400.
GenBank Database: AEP08879.1, Jan. 31, 2014. pp. 1-2.
GenBank Database: AGO38582.1, Jan. 31, 2014, pp. 1-2.
GenBank Database: EDG23390.1, Apr. 6, 2007, pp. 1-2.
Golodne, D., Brazilian preliminary office action issued in Brazilian Patent Application No. BR112018005318-0 published in Brazilian Industrial Property Journal No. 2601 of Nov. 10, 2020, with English language translation pages).
Huning, Z., Chinese Office Action issued in Chinese Patent Application No. 201680054495.3, dated Dec. 10, 2020, with English language translation (25 pages).
International Search Report for PCT/US2016/052338, dated Mar. 29, 2017.
English-language translation of the Israeli Office Action issued in Israeli Patent Application No. 258122 dated Feb. 27, 2019, pp. 1-3.
Lai et al., Antibacterial activity of Acinetobacter baumannii phage pAB2 endolysin (LysAB2) against both Gram-positive and Gram-negative bacteria, Appl. Microbiol Biotechnol 2011; 90:529-539.
Loeffler et al.,Synergistic Lethal Effect of a Combination of Phage Lytic Enzymes with Different Activities on Penicillin-Sensitive and -Resistant *Streptococcus pneumoniae* Strains, Antimicrob Agents Chemother. 2003; 47(1): 375-377.
NCBI Database Reference Sequence: WP_014102102.1, May 18, 2013, p. 1.
NCBI Database Reference Sequence: YP_001293410.1, Jun. 18, 2007, p. 1.
Office Action issued in Japanese Patent Application No. 2018-513835 dated Jul. 8, 2020 with English language translation (12 pages).

(56) References Cited

OTHER PUBLICATIONS

EESR issued in European Patent Application No. 16778940.3 dated Oct. 21, 2020 (3 pages).
Pakula, A.A. et al., Genetic analysis of protein stability and function, Annu. Rev. Genet., vol. 23 (1989) pp. 289-310.
Severin, E.S. (Editor), Biokhimika: Textbook—2nd revised ed.—Moskva: GEOTAR-MED, 2004, (Series "XXI vek"), p. 9.
Shibahara, N., Japanese Office Action issued in Japanese Patent Application No. 2018-513835 dated Mar. 16, 2021 with English language translation (6 pages).
English-language translation of the Russian Office Action issued in Russian Patent Application No. 2018107245/10(011078) dated Oct. 23, 2019, pp. 1-7.
Russian Office Action issued in Russian Application No. 2018107245/10 dated May 27, 2019, pp. 1-13, with English translation.
Svenson, J. et al., Albumin binding of Short Cationic Antimicrobial Micropeptides and its influence on the in Vitro Bactericidal Effect, J. Med. Chem. 2007; 50 (14):3334-3339.
UniProtKB Database: B5WZU3, Nov. 25, 2008, pp. 1-5.
First Examination Report issued in Indian Patent Application No. 201817008090 dated May 24, 2021, with English language translation (5 pages).
Huning, Z., Chinese Office Action issued in Chinese Patent Application No. 201680054495.3 dated May 8, 2021 with English language translation (26 pages).
Australian Examination Report issued in Australian Patent Application No. 2016324298, dated Sep. 22, 2021 (5 pages).
Mexican Office Action issued in Mexican Patent Application No. MX/a/2018/003101, dated Oct. 11, 2021, with English-language translation (13 pages).
Whisstock, et al., Prediction of protein function from protein sequence and structure, Quarterly Review of Biophysics 2003, 36(3):307-340.
Witkowski, et al., Conversion of a beta-ketoacyl synthase to a malonyl decarboxylase by replacement of the active-site cysteine with glutamine, Biochemistry 1999, Sep. 7, 38(36):11643-50.
Vouillamoz, et al., Bactericidal synergism between daptomycin and phage lysin Chp-1 in mouse model of pneumococcal bacteraemia, International J. Antimicrobial Agents 2013, 42:416-421.
Japanese Decision of Final Rejection issued in Japanese Patent Application No. 2018-513834, dated Jul. 20, 2021, with English language translation (9 pages).
Second Chinese Office Action issued in Chinese Patent Application No. 201680054182.8, dated Jul. 6, 2021, with English language translation (15 pages).
Brazilian preliminary office action issued in Brazilian Patent Application No. BR112018005316-3 dated Oct. 27, 2020, with English language translation (6 pages).
Briers, Y. et al., "Use of bacteriophage endolysin EL188 and outer membrane permeabilizers against Pseudomonas aeruginosa", Journal of Applied Microbiology 2011, 10(3):778-785.
Morita, M. et al., "Functional analysis of antibacterial activity of Bacillus amyloliquefaciens phage endolysin against Gram-negative bacteria", FEBS Letters 2001, 500(1-2):56-59.
Andreu, D., "Identification of an anti-mycobacterial domain in NK-lysin and granulysin", Biochemical Journal 1999, 344:845-849.
Farris, et al., "Mitrecin A, an endolysin-like bacteriolytic enzyme from a newly isolated soil streptomycete", Letters in Applied Microbiology 2014, 58(5):493-502.
Wang, Z. et al., "Genomic insights into an obligate epibiotic bacterial predator: Micavibrio aeruginosavorus ARL-13", BMC Genomics, 2011, 12(1):453.
Pastagia, M., et al., "Lysins: the arrival of pathogen-directed anti-infectives", J. Med. Microbio. 2013, 62 (Pt_10):1506-1516.
Lukacik, P. et al., "Structural engineering of a phage lysin that targets Gram-negative pathogens", Proceedings of the National Academy of Sciences 2012, 109(25):9857-9862.
Lukacik, P. et al., "Using a bacteriocin structure to engineer a phage lysin that targets Yersinia pestis", Biochemical Society Transactions 2012, 38(6):1503-1506.
Chinese office action issued in Chinese Patent Application No. 201680054182.8 dated Nov. 9, 2020, with English language translation (12 pages).

* cited by examiner

B. MSSA strain ATCC 29213

A. MRSA strain MW2

C. VISA strain ATCC 700699

USE OF LYSIN TO RESTORE/AUGMENT ANTIBACTERIAL ACTIVITY IN THE PRESENCE OF PULMONARY SURFACTANT OF ANTIBIOTICS INHIBITED THEREBY

STATEMENT OR RELATED APPLICATIONS

This patent application claims the priority of U.S. Provisional Patent Application 62/220,212 filed Sep. 17, 2015, and U.S. Provisional Patent Application 62/247,619 filed Oct. 28, 2015; the contents of these provisional applications are hereby incorporated by reference in their entirety.

BACKGROUND OF THE DISCLOSURE

Technical Field

The present disclosure relates to the field of combatting bacterial infection, specifically of the respiratory tract and more specifically of the lower respiratory tract, notably tissues and organs the epithelium of which is characterized by the presence of pulmonary surfactant. The disclosure more addresses a problem of reduced effectiveness of antibiotics in combatting infection due to factors in the environment of the infection, such as the pulmonary surfactant, rather than to antibiotic resistance developments.

Description of the Related Art

Bacteriophage lysin polypeptide CF-301 is a first-in-class antimicrobial agent under development to treat *Staphylococcus aureus* bacteremia and endocarditis. Hallmark features of CF-301 include rapid pathogen-specific bacteriolysis, an absence of resistance, synergy with standard-of-care antibiotics and anti-biofilm activity (Schuch et al., *J Infect Dis.;* 209(9):1469-78 (2014). doi: 10.1093/infdis/jit637. Epub 2013 Nov. 28.). CF-301 is the first lysin to enter FDA-regulated clinical trials. CF-301 (PlySs2) has the amino acid sequence depicted in SEQ ID NO: 1 (GenBank accession ZP 03625529) and has been described in U.S. Pat. No. 9,034,322.

Other lysins active against Staphylococci responsible for airway or respiratory tract infections include without limitation PlyC, PlyGBS, LysK, lysostaphin, chimeric lysin ClyH, (Cheng et al. *Antimicrob Agents Chemother.* 49(1): 111-117 (2005); McGowan et al. Proc Natl Acad Sci USA., 109(31):12752-7 (2012), Becker et al. FEMS Microbiol Lett., 287(2):185-91 (2008), Yang et al. *Antimicrob Agents Chemother.* 2014; 58(1):536-42 (2014). Lysin polypeptides active against *Streptococcus pneumoniae* include PAL and Cpl1 lysins described respectively in WO 2008/00132 (including the sequence of the CHAP domain for chimerization) and CN 102021161 (Garcia et al. J Virol. 61(8):2573-80 (1987); Varea et al. J Biol Chem.,279(42):43697-707. (2004)). The disclosures of the foregoing patents and references are incorporated by reference in their entirety for all purposes. Several other lysins active against a variety of bacterial pathogens, including bacteria responsible for infections of the airways and more particularly the lower respiratory tract, have been identified.

The cyclic lipopeptide antibiotic daptomycin has been approved for skin and skin structure infections. Daptomycin is rapidly bactericidal against gram-positive (G+) bacteria and it exerts its activity by insertion into and disruption of the functional integrity of the G+ plasma membrane, a mechanism strongly dependent on the presence of physiologic levels of free calcium. However, daptomycin has failed to meet criteria in a clinical trial for severe community-acquired pneumonia. This deficiency has been shown to be due to an interaction between daptomycin and pulmonary surfactant, which inhibits the activity of this antibiotic specifically in the lung environment and more generally in the airway environment wherein pulmonary surfactant is present. Surfactant Inhibition of Daptomycin, Silverman, J. A. et al, *JID*, 191: 2149-2152 (2005). Thus, daptomycin is not indicated for treatment of lung and more generally airway (especially lower respiratory tract) infections and those of skill in the art would not employ a treatment regimen including daptomycin to treat such infections. The inability of daptomycin to combat infection in the presence of pulmonary surfactants been shown dramatically in Koplowicz et al. *Clin Infect Dis.* 49(8):1286-7 (2009). Recent studies have focused on overcoming daptomycin inactivity in the presence of surfactant by testing and evaluating antibacterial activity of hybrid molecules of the structurally related lipopeptide A54145 (Nguyen et al. *Antimicrob Agents Chemother.* 2010 April; 54(4): 1404-1413.)

Pulmonary surfactant, a primary component of epithelial lining fluid, is a complex lipid-and-protein mixture that coats the interior surface of the airway, reducing surface tension within the alveoli. Surfactant is composed primarily of dipalmitoylphosphatidylcholine (~80% in all mammalian species), along with significant amounts of phosphatidylglycerol (PG) and smaller amounts of minor phospholipids, neutral lipids, and cholesterol. There are 4 protein components: hydrophilic proteins SP-A and SP-D and hydrophobic proteins SP-B and SP-C. Goerke J. Pulmonary surfactant: functions and molecular composition. *Biochim Biophys Acta* 1998; 1408:79-89. Daptomycin is inserted into artificial membrane vesicles composed of phosphatidylcholine (PC) and PC/PG. Lakey J H, et al: Fluorescence indicates a calcium-dependent interaction between the lipopeptide antibiotic LY146032 and phospholipid membranes. *Biochemistry* 1988; 27:4639-45; Jung D, et al. Structural transitions as determinants of the action of the calcium-dependent antibiotic daptomycin. *Chem Biol* 2004; 11:949-57.

A major problem in medicine has been the development of drug resistant bacteria as more antibiotics are used for a wide variety of illnesses and other conditions. Hospital infections are the 8th leading cause of death in the United States, due in large part to drug-resistant and newly-emerging pathogens. For example, there are over 500,000 cases of *Staphylococcus aureus* annually in the U.S. and over 65% of strains are multidrug resistant (for example certain strains of methicillin-resistant *S. aureus* (MRSA) are also multidrug resistant. The use of more antibiotics and the number of bacteria showing resistance has prompted longer treatment times. Furthermore, broad, non-specific antibiotics, some of which have detrimental effects on the patient, are now being used more frequently. A related problem with this increased use is that many antibiotics do not penetrate mucus linings easily, or are inhibited by factors present in these linings as discussed above. Additionally, the number of people allergic to antibiotics appears to be increasing. Accordingly, there is a commercial need for new antibacterial approaches, especially those that operate via new modalities or provide new or improved means to kill pathogenic bacteria and thereby treat infection.

The discovery of lysin polypeptides, enzymes derived from bacteriophage that can penetrate the bacterial wall or outer membrane and directly lyse bacteria or expose them to bactericidal agents, such as the host's immune system and/or antibiotics, has been a breakthrough in the field of infectious disease. In particular, lysins administered in conjunction with antibiotics have been found to synergize with them, resulting in an increase in the effectiveness of antibiotics against even resistant pathogens. This synergy has opened the way for use of reduced doses of the antibiotic and/or the lysin, reducing the potential for side effects. See, e.g., U.S. Pat. No. 9,034,322.

However, where an antibiotic has been found ineffective in treating a particular infection caused by an otherwise susceptible pathogen because of environmental factors, such as surfactant inhibition, rather than resistance, the use of lysins has not been previously proposed. Indeed, there was no reason to expect that lysins would improve effectiveness of antibiotics in the face of inhibition by pulmonary surfactant. Accordingly, the effectiveness of the methods disclosed below was unexpected.

Gram-positive bacteria are surrounded by a cell wall containing polypeptides and polysaccharide. The gram-positive cell wall appears as a broad, dense wall that is 20-80 nm thick and consists of numerous interconnecting layers of peptidoglycan. Between 60% and 90% of the gram-positive cell wall is peptidoglycan, providing cell shape, a rigid structure, and resistance to osmotic shock. The cell wall does not exclude the Gram stain crystal violet, allowing cells to be stained purple, and therefore "Gram-positive." Gram-positive bacteria include but are not limited to the genera *Actinomyces, Bacillus, Listeria, Lactococcus, Staphylococcus, Streptococcus, Enterococcus, Mycobacterium, Corynebacterium*, and *Clostridium*. Medically relevant species include *Streptococcus pyogenes, Streptococcus pneumoniae, Staphylococcus aureus*, and *Enterococcus faecalis*. *Bacillus* species, which are spore-forming, cause anthrax and gastroenteritis. Spore-forming *Clostridium* species are responsible for botulism, tetanus, gas gangrene and pseudomembranous colitis. *Corynebacterium* species cause diphtheria, and *Listeria* species cause meningitis. *Staphylococcus aureus* and *Streptococcus pneumoneae* are two major causative agents for pneumonia, whether community-acquired, nosocomial, secondary to aspiration or opportunistic.

Thus, to the extent that otherwise effective antibiotics are inhibited by factors present in the organ or tissue that is the site of the infection, such as pulmonary surfactant in the case of infections of the lungs or other airways and more generally of the respiratory tract, a treatment regimen that would restore and even augment activity of such antibiotics would be of great commercial and public health value.

In addition to daptomycin discussed above, other antibiotics that are known to be inhibited by pulmonary surfactant include without limitation: tobramycin, an aminoglycoside used to treat infections caused by the gram-negative bacterium *Pseudomonas aeruginosa* a common cause of pneumonia (van 't Veen A et al. *Antimicrob. Agents Chemother.* 39:329-333 (1995)), and colistin, a cyclic lipopeptide (polymixin) broadly active against gram-negative bacteria, including *P. aeruginosa*. Schwameis, R. et al, Effect of Pulmonary Surfactant on Antimicrobial Activity In Vitro, October 2013 Volume 57 Number 10 *Antimicrobial Agents and Chemotherapy* p. 5151-5154.

SUMMARY OF THE DISCLOSURE

In one aspect, the present disclosure relates to a method for treating a subject afflicted with a bacterial infection of an organ or tissue in which pulmonary surfactant is present, the method comprising regardless of order the following steps:
 a. administering to the subject a first amount of an antibiotic having antibacterial activity against the bacteria responsible for the infection which activity is inhibited by the pulmonary surfactant;
 b. co-administering to the subject a second amount of a lysin polypeptide
wherein said first and second amount in combination are effective to kill the bacteria responsible for the infection and thereby treat the infection.

In some embodiments, the lysin has antibacterial activity against the bacteria responsible for the infection.

In some embodiments, the first amount is such that it would be ineffective to treat the infection if the antibiotic were administered as monotherapy.

In some embodiments, the antibiotic is a cyclic lipopeptide or an aminoglycoside.

In a more particular embodiment the lysin polypeptide has the amino acid sequence of SEQ ID NO: 1 or variants thereof having antibacterial activity against *Staphylococcus aureus* and at least 80% sequence identity to SEQ ID NO: 1, and the bacterium responsible for the infection is *Staphylococcus aureus*.

In some embodiments the *S. aureus* is MRSA MSSA or VISA.

In some embodiments, the antibiotic is a cyclic lipopeptide, for example daptomycin.

In other embodiments the antibiotic is an aminoglucoside, for example tobramycin.

In some embodiments, the second amount or the first amount is a subthreshold amount (or both amounts are subthreshold).

In some embodiments, the lysin polypeptide is administered parenterally or by inhalation; in some embodiments, the antibiotic is administered orally or parenterally or by inhalation.

In some embodiments, the subject is a mammalian subject.

In some embodiments, the lysin polypeptide is PAL or Cpl-1 and the bacterium responsible for the infection is *Streptococcus pneumoniae*.

In some embodiments, the bacterium responsible for the infection is gram-negative, for example, *P. aeruginosa*.

In some embodiments, lysin is an artilysin described in one or more of the following patent applications: US 20140120074, WO/2015/070912; WO/2015/071436; WO/2015/070911; WO/2015/071437; US 20150118731 and WO/2012/085259 or is a GN lysin having a sequence selected from the group of Artilysins, described in one or more of the following patent applications: US 20140120074, WO/2015/070912; WO/2015/071436; WO/2015/070911; WO/2015/071437; US 20150118731 and WO/2012/085259 and the following gram-negative lysins disclosed in U.S. Provisional Patent Application 62/247,619 filed Oct. 28, 2015, copy of which is attached to this patent application as Appendix A, and which is incorporated by reference in its entirety: GN37 (SEQ ID NO: 6); GN2 (SEQ ID NO: 7); GN4 (SEQ ID NO: 8); GN14 (SEQ ID NO: 9); GN43 (SEQ ID NO: 10); PGN4 (SEQ ID NO: 11); FGN4-1 (SEQ ID NO: 12); FGN4-2 (SEQ ID NO: 13); FGN4-3 (SEQ ID NO: 14); and FGN4-4 (SEQ ID NO: 15).

In various more specific embodiments, the antibiotic is a cyclic lipopeptide such as colistin or an aminoglycoside such as tobramycin.

In another aspect, the disclosure relates to a method for treating a subject afflicted with a streptococcus or staphylococcus bacterial infection of the lower respiratory tract in which pulmonary surfactant is present, the method comprising regardless of order the following steps:

a. administering to the subject a first amount of an antibiotic having antibacterial activity against the bacteria responsible for the infection which activity is inhibited by the pulmonary surfactant;
    i. co-administering to the subject a second amount of at least one lysin polypeptide, selected from the group consisting of: CF-301, ClyS, lysostaphin, LysK, Sal-200, LysGH15, PlyV12, ClyH, MV-L, Ply, PlyPly, PlyGBS, LambdaSa1, LambdaSa2, Cpl1, Pal, active fragments thereof, and chimeric combinations thereof wherein the binding domain of one of the foregoing lysins or fragments has been fused to the catalytic domain of another wherein said first and second amount in combination are effective to kill the bacteria responsible for the infection and thereby treat the infection.

In some embodiments, the antibiotic is daptomycin.

A method for restoring or augmenting bactericidal activity of an antibiotic in an organ or tissue in which pulmonary surfactant is present in an amount that is or would be inhibitory of the activity of the antibiotic against a bacterial infection in said organ or tissue, the method comprising: administering to a subject afflicted with an infection of said organ or tissue a first amount of said antibiotic and co-administering to the subject a second amount of a lysin polypeptide having antibacterial activity against the bacterium responsible for the infection, wherein administration of the lysin overcomes or sidesteps the inhibition, the amounts in combination being effective to kill said bacterium and thereby treat the infection.

BRIEF DESCRIPTION OF THE DRAWINGS

FIG. 1 shows MIC values for CF-301 and DAP against MRSA strain MW2 (FIG. 1A), MSSA strain ATCC 29213 (FIG. 1B), and VISA strain ATCC 700699 (FIG. 1C).

In FIG. 4A, scale bars are 0.5 µm. In FIG. 4B, scale bars are 2 µm (5,000× images) and 1 µm (20,000× images).

DETAILED DESCRIPTION

Figure 1:
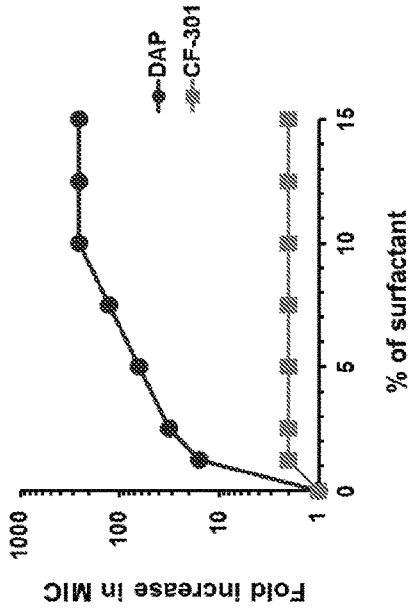
FIG. 1 demonstrates that CF-301 is active in bovine-derived surfactant while DAP is not active.
Figure 1:
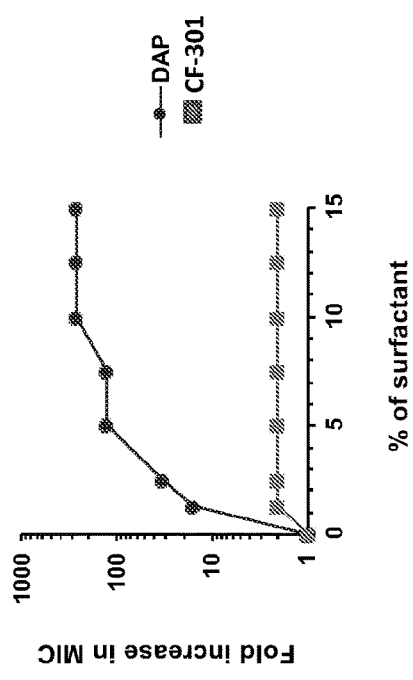
Figure 1:
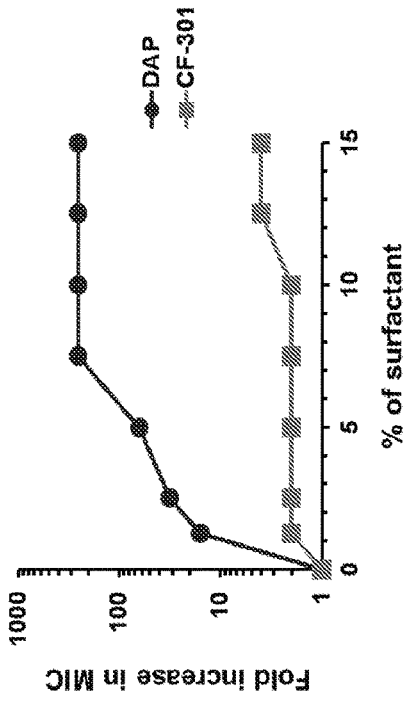

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Definitions

The following terms and phrases include the meanings provided below unless the context clearly indicates otherwise.

The term "treatment" refers to any process, action, application, therapy, or the like, wherein a subject, including a human being, is subjected to medical aid with the object of providing a treatment for or curing a disorder, or killing or eradicating a pathogen, or improving the subject's condition, directly or indirectly. Treatment also refers to reducing incidence, or alleviating symptoms, eliminating recurrence, preventing recurrence, preventing incidence, improving symptoms, improving prognosis or combinations thereof. "Treatment" further encompasses reducing the population, growth rate or virulence of the bacteria in the subject and thereby controlling or reducing a bacterial infection in a subject or bacterial contamination of an organ or tissue or environment. Thus "treatment" that reduces incidence is effective to inhibit growth of at least one Gram-positive or of at least one Gram-negative bacterium in a particular milieu, whether it be a subject or an environment. On the other hand "treatment" of an already established infection or contamination refers to reducing the population or killing, including even eradicating Gram-positive or Gram-negative bacteria responsible for an infection or contamination.

"Preventing" includes the prevention of the incidence, recurrence, spread, onset or establishment of a disorder such as a bacterial infection. It is not intended that the present disclosure be limited to complete prevention or to prevention of establishment of an infection. In some embodiments, the onset is delayed, or the severity of a subsequently contracted disease is reduced, and such constitute examples of prevention. Contracted diseases in the context of the present disclosure encompass both those manifesting with clinical or subclinical symptoms, such as the detection of as well as the detection of growth of a bacterial pathogen when symptoms associated with such pathologyare not yet manifest.

The term "effective amount" refers to an amount which, when applied or administered in an appropriate frequency or dosing regimen, is sufficient to prevent or inhibit bacterial growth or prevent, reduce or ameliorate the onset, severity, duration or progression of the disorder being treated (here bacterial pathogen growth or infection), prevent the advancement of the disorder being treated, cause the regression of the disorder being treated, or enhance or improve the prophylactic or therapeutic effect(s) of another therapy, such as antibiotic or bacteriostatic therapy.

"Co-administer" is intended to embrace separate administration of a lysin polypeptide and an antibiotic or any other antibacterial agent in a sequential manner as well as administration of these agents in a substantially simultaneous manner, such as in a single mixture/composition or in doses given separately, but nonetheless administered substantially simultaneously to the subject, for example at different times in the same day or 24-hour period (or in a shorter or longer interval as long as the administration of the antibiotic benefits from the conjoint administration of the lysin). Such co-administration of lysin polypeptides with one or more additional antibacterial agents such as antibiotics can be provided as a continuous treatment lasting up to days, weeks or months. Additionally, the co-administration need not be continuous or co-extensive as long as the inhibition of the administered antibiotic by pulmonary surfactant is abated and effectiveness of the antibiotic in treating infections of an organ or tissue wherein pulmonary surfactant is present is restored or augmented.

"Subject" refers to a subject to be treated and includes inter alia a mammal, including without limitation a human, a plant, a lower animal, a single cell organism or a cell culture. For example, the term "subject" is intended to include organisms, e.g., prokaryotes and eukaryotes, which are susceptible to or afflicted with Gram-negative or Gram-positive bacterial infections. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or susceptible to a bacterial infection, whether such infection be systemic or confined to a particular organ or tissue.

"Polypeptide" is used interchangeably with the term "protein" and "peptide" and refers to a polymer made from amino acid residues and having at least about 30 amino acid residues. The term includes not only polypeptides in isolated form, but also active fragments and derivatives thereof (defined below). The term "polypeptide" also encompasses fusion proteins or fusion polypeptides comprising a lysin polypeptide as described below and maintaining the lysin function. A polypeptide can be a naturally occurring polypeptide or an engineered or synthetically produced polypeptide. A particular lysin polypeptide can be, for example, derived or removed from a native protein by enzymatic or chemical cleavage, or can be prepared using conventional peptide synthesis techniques (e.g., solid phase synthesis) or molecular biology techniques (such as those disclosed in Sambrook, J. et al., Molecular Cloning: A Laboratory Manual, Cold Spring Harbor Press, Cold Spring Harbor, N.Y. (1989)) or can be strategically truncated or segmented yielding active fragments, as illustrated for example herein with a fragment of GN4 comprising the amphipathic domain of GN4 and further truncated versions thereof maintaining lysin activity against the same or at least one common target bacterium (see Appendix A). Variants of native lysin polypeptides are also encompassed having at least 80% or at least 85% or at least 90% or at least 95% or at least 98% sequence identity with the native lysin polypeptide (which, as stated above includes active fragments of a native lysin protein).

"Bactericidal" in the context of an agent or a compound conventionally means having the property of causing the death of bacteria or capable of killing bacteria to an extent of at least a 3-log (99.9%) or better reduction among an initial population of bacteria.

"Augmenting" within the context of the present disclosure means that a degree of antimicrobial activity of an antibiotic is higher than it would be in the presence of pulmonary surfactant. For example, antibiotic activity in the context of the present disclosure can be restored or augmented by at least 5 fold, at least 10 fold, at least 16 fold, at least 20 fold, at least 24 fold, at least 30 fold, at least 40 fold, at least 50 fold, at least 70 fold, at least 80 fold at least 100 fold, more than 10 fold, more than 20 fold, more than 50 fold, more than 100 fold. Additionally, in the context of the present disclosure, the activity of lysin can be augmented by at least 2 fold, at least 4 fold, at least 8 fold, at least 10 fold, up to 10 fold, up to 16 fold, up to 20 fold, more than 2 fold, more than 4 fold, more than 8 fold, more than 10 fold, more than 20 fold.

"Inhalable" refers to a method of direct delivery of a composition to the respiratory tract during or in conjunction with routine or assisted respiration (e.g., by intratracheobronchial, pulmonary, and/or nasal administration). Inhalable formulations include, but are not limited to atomized, nebulized, dry powder and/or aerosolized formulations.

"Biofilm" refers to an aggregate of bacteria that are embedded within a self-produced matrix of polysaccharides, glycoproteins or nucleic acids. In this state, bacteria are highly resistant to antibiotics.

Embodiments

In some embodiments, the present disclosure describes combining CF-301 with the antibiotic daptomycin (DAP) to expand the indications for both drugs to infections of an organ or tissue, such as infections of the airways, wherein pulmonary surfactant is present. In some embodiments, the pulmonary surfactant is expressed in organs or tissues other than respiratory system (Madsen et al. *Am J Respir Cell Mol Biol.*, 29(5):591-7 (2000)). While DAP is a potent therapeutic option for bacteremia and endocarditis, it cannot be used for pulmonary infections because of selective inhibition by pulmonary surfactant (Silverman et al., *J Infect Dis.*, 191 (12):2149-52. (2005)). In light of clinical limitations associated with surfactant-mediated inhibition of DAP, the present disclosure describes that CF-301 restores or augments DAP activity in the lung (and other portions of the respiratory tract wherein pulmonary surfactant is present including for example the bronchial passages but also the trachea and pharynx), wherein DAP activity is normally inhibited by pulmonary surfactant and as such offers a new option for treating airway and notably lower respiratory tract infections, such as staph pneumonia, bronchial pneumonia, pneumococcal pneumonia and atypical pneumonia.

More broadly, the present disclosure describes that inhibition of antibiotics due to environmental factors, such as the presence of pulmonary surfactant in an organ or tissue such as the respiratory epithelium can be sidestepped or overcome and the effectiveness of the antibiotic in that milieu restored or augmented by co-administration of an antibiotic and a lysin.

The antibiotic may be one to which the causative agent of the infection to be treated is normally susceptible; the lysin may be one which is active against the same organism. Typically, the antibiotic will be administered in a first amount, such as one which would be an effective amount when used as monotherapy in the absence of the surfactant or a smaller amount including in certain embodiments a subthreshold amount, since the antibiotic will be substantially freed from interference by the surfactant and available to synergize with the lysin. Thus the antibiotic amount to be employed will be subject to fine-tuning which is well within the skill of the art. The lysin will typically be administered in a second amount, such as one that would be employed if the lysin were used as monotherapy, or a smaller amount, including in certain embodiments a subthreshold amount since the lysin and the antibiotic synergize. Again, the amount of the lysin will be subject to optimization which is well within the skill of the art. The first and second amounts will be such that at least in combination (if not also individually) will be effective to kill bacteria responsible for the infection and thereby treat the infection, thereby eradicating it or contributing to its partial or complete eradication.

In one embodiment, the lysin is administered in a first amount, and the antibiotic is administered in a second amount.

The antibiotic may be administered by any appropriate route, such as parenteral, oral or in certain cases by inhalation. The lysin may be administered by any appropriate route, by injection (parenterally) or by inhalation. The duration of therapy will be determined by assessment of the effectiveness of the treatment, such as by the attenuation and/or disappearance of symptoms, the reduction or elimination of pathogen titers, the improvement in the physical condition of the treated subject, etc., as well as by the rate of improvement in one or more of such assessment parameters. There may well be variation from subject to subject depending on such factors as age, type of infection, attending complications and general physical condition of the patient. The normal duration of antibiotic monotherapy will be a bench mark for determining the duration of the conjoint therapy according to the present disclosure.

Due to the presence of pulmonary surfactant, the interior of the airway has a unique environment within the body. Studies have shown that in certain instances, organ-specific inhibition of an antibiotic can occur, resulting in inefficacy of a particular antibiotic in that specific organ. Such organ-specific inhibition has been observed in the case of daptomycin (DAP), wherein small amounts of pulmonary surfactant were capable of inhibiting DAP activity against *Staphylococcus aureus*, rendering DAP not suitable for the treatment of pulmonary infections caused by this pathogen (Silverman et al., *J Infect Dis.,* 191(12):2149-52. (2005)). Studies by Silverman et al. were further corroborated in a patient treated with DAP for bronchoalveolar pneumonia due to *S. aureus* (Koplowicz et al. *Clin Infect Dis.* 49(8): 1286-7 (2009)). Both studies (Silverman et al., and Koplowicz et al.) established that the presence of pulmonary surfactants hampers the antimicrobial action of DAP. Based on this, it is anticipated that DAP will be active and available to treat infections that are due to other respiratory pathogens provided that DAP is active against such pathogens in the absence of pulmonary surfactant (e.g., in vitro or when the infection is established in an organ or tissue devoid or substantially devoid of pulmonary surfactant). Nonlimiting examples of such pathogens are coagulase negative staphylococci, *Streptococcus pneumoniae* and *Streptococcus pyogenes*.

In addition to DAP, which belongs to a class of cyclic lipopeptide antibiotics, pulmonary surfactant-induced inhibition of antibiotic activity has been observed for additional antibiotics, such as colistin, a lipopetide, and tobramycin, an aminoglycoside. Thus, the methods of the present disclosure can be used to restore or augment activity of these antibiotics against susceptible bacterial pathogens, wherein such pathogens infect an organ or tissue where pulmonary surfactant is present.

Currently, DAP is indicated for the treatment of complicated skin and skin structure infections (cSSSI) caused by susceptible isolates of the following Gram-positive bacteria: *Staphylococcus aureus* (including methicillin-resistant isolates), *Streptococcus pyogenes, Streptococcus agalactiae, Streptococcus dysgalactiae* subsp. *equisimilis*, and *Enterococcus faecalis* (vancomycin-susceptible isolates only). DAP is also used in the treatment of *Staphylococcus aureus* bloodstream infections, including those with right-sided infective endocarditis, caused by methicillin-susceptible and methicillin-resistant isolates. Furthermore, in vitro studies have shown that penicillin resistant *Streptococcus pneumoniae* is inhibited by DAP (Piper et al. J Infect Chemother (2005) 11:207-209).

In one embodiment, the present disclosure provides methods for restoring or augmenting surfactant-inhibited antibiotic activity comprising administering a combination of a lysin and one or more antibiotic to an organ or a tissue wherein pulmonary surfactant is present. Since pulmonary surfactants are present in lung tissue, and the present disclosure provides in vitro and in vivo evidence of lysin's ability to restore the antimicrobial activity of surfactant-inhibited antibiotic, it is anticipated that other bacteria that cause infections of the lower respiratory tract will be killed by combinations of DAP and lysins active against these bacteria.

It shall be understood that the lysins exemplified herein including in Tables 1 through 3 can be replaced by active fragments thereof and chimeric combinations of the binding domain of one lysin with the catalytic domain of another. See, e.g., Cheng et al. *Appl Microbiol Biotechnol.* 74(6): 1284-91 (2007). Indeed some of the examples are already fragments or chimeric lysin polypeptides.

TABLE 1

Examples of: bacteria susceptible to DAP treatment (in the absence of pulmonary surfactant), types of infection that occur in the presence of pulmonary surfactant, and lysin compound(s) capable of killing or inhibiting the growth of each bacteria listed.

| Bacteria | Type of Infection | Lysin capable of inhibiting the growth of said bacteria |
|---|---|---|
| *Staphylococcus aureus* | respiratory tract infections, pneumonia | CF-301 (SEQ ID NO: 1), ClyS (SEQ ID NO: 2), lysostaphin, LysK (SEQ ID NO: 4) [GenBank: AFN38929.1], Sal-200 and LysGH15 (which are derivatives of LysK), PlyV12 (SEQ ID NO: 3), ClyH, and MV-L[GenBank: AB254389.1]. |
| *Streptococcus pyogenes* | infections of the upper respiratory tract, pneumonia (Steer et al. *Drugs*. 2012 Jun. 18; 72(9): 1213-27). | CF-301 (Gilmer et al. Antimicrob. Agents Chemother. June 2013 vol. 57 no. 6 2743-2750)<br>PlyC (Nelson et al. Proc Natl Acad Sci USA. 2006 Jul. 11; 103(28): 10765-10770.)<br>PlyGBS (Cheng et al. Antimicrob Agents |

TABLE 1-continued Examples of: bacteria susceptible to DAP treatment (in the absence of pulmonary surfactant), types of infection that occur in the presence of pulmonary surfactant, and lysin compound(s) capable of killing or inhibiting the growth of each bacteria listed.

| Bacteria | Type of Infection | Lysin capable of inhibiting the growth of said bacteria |
|---|---|---|
| | | Chemother. 2005 January; 49(1): 111-117.), PlyGBS mutants (Cheng et al. *Appl Microbiol Biotechnol.* 74(6): 1284-91 (2007) PlyPly (Lood et al. Antimicrob Agents Chemother. 2014 June; 58(6): 3073-3084.) |
| *Streptococcus agalactiae* | infections of the upper respiratory tract, pneumonia | CF-301 (Schuch et al. J Infect Dis. 2014 May 1; 209(9): 1469-1478.) LambdaSa1, LambdaSa2 (Pritchard et al. Appl Environ Microbiol. 2007 November; 73(22): 7150-7154. |
| *Streptococcus dysgalactiae* subsp. *equisimilis* | Infections of the upper respiratory tract, pneumonia (Preziuso et al. J Vet Sci. 2010 March; 11(1): 67-72.) | PlySK1249 (Oechslin et al. *Antimicrob Agents Chemother.* 2013 December; 57(12): 6276-6283) |
| vancomycin-resistant *Enterococcus faecalis* | respiratory infections, pneumonia | PlyV12 (SEQ ID NO: 3) |
| *Streptococcus pneumoniae* | respiratory infections, pneumonia | Cpl-1 (SEQ ID NO: 5) [NC_001825.1], dimerized forms of Cpl-1, Pal (Fenton et al. Bioeng Bugs. 2010 January-February; 1(1): 9-16.) |

The entire disclosure of all documents cited in the above table are incorporated by reference in their entirety for all purposes.

The aminoglycoside class of antibiotics comprises many different agents. Gentamicin, tobramycin, amikacin, streptomycin, neomycin, and paromomycin are approved by the US Food and Drug Administration (FDA). Tobramycin is active against various Gram-negative bacteria, including, but not limited to *P. aeruginosa, E. coli, Acinetobacter* spp., *Citrobacter* spp., *Enterobacter* spp. and other. In particular, tobramycin displays high activity against *P. aeruginosa*, a common causative agent of pneumonia, both community acquired and nosocomial.

In terms of Gram-positive bacteria, tobramycin exhibits a narrower spectrum of activity, wherein with the exception of *S. aureus* and *S. epidermidis*, most Gram-positive bacteria are resistant to tobramycin. However, similar to DAP, tobramycin activity against *Klebsiella pneumoniae, Pseudomonas aeruginosa, S. aureus,* and *S. pneumoniae* is reduced in the presence of surfactant (van 't Veen A et al. *Antimicrob. Agents Chemother.* 39:329-333 (1995)). Infections associated with *Klebsiella pneumoniae, Pseudomonas aeruginosa, S. aureus,* and *S. pneumoniae* and lysins active against these bacteria are listed in Table 2.

Thus, the methods of the present disclosure can be used for restoring or augmenting surfactant-inhibited antibiotic activity in order to treat infections caused by Gram positive bacteria, or Gram negative bacteria, or both. Commonly, infections are polymicrobial, with mixed Gram-positive and Gram-negative species (Citron et al. *J Clin Microbiol.* 45(9): 2819-2828 (2007)). In some embodiments, the methods of the present disclosure can be used for restoring or augmenting surfactant-inhibited antibiotic activity in order to treat a polymicrobial infection.

TABLE 2

Examples of: bacteria susceptible to tobramycin treatment (in the absence of surfactant), types of infection that occur in the presence of pulmonary surfactant, and lysin compound(s) capable of killing or inhibiting the growth of each bacterium listed.

| Bacteria | Infection | Lysin capable of inhibiting the growth of said bacteria |
|---|---|---|
| *Klebsiella pneumoniae* | pneumonia; lower respiratory tract infections | Artilysins, described in one or more of the following patent applications: U.S. 20140120074, WO/2015/070912; WO/2015/071436; WO/2015/070911; WO/2015/071437; U.S. 20150118731 and WO/2012/085259 GN37 (SEQ ID NO: 6) GN2 (SEQ ID NO: 7) GN4 (SEQ ID NO: 8) GN14 (SEQ ID NO: 9) GN43 (SEQ ID NO: 10) PGN4 (SEQ ID NO: 11) FGN4-1 (SEQ ID NO: 12) FGN4-2 (SEQ ID NO: 13) FGN4-3 (SEQ ID NO: 14) FGN4-4 (SEQ ID NO: 15) |
| *Pseudomonas aeruginosa,* | respiratory system infections, pneumonia | Artilysins, described in one or more of the following patent applications: U.S. 20140120074, WO/2015/070912; WO/2015/071436; WO/2015/070911; WO/2015/071437; U.S. 20150118731 and WO/2012/085259 |

TABLE 2-continued

Examples of: bacteria susceptible to tobramycin treatment (in the absence of surfactant), types of infection that occur in the presence of pulmonary surfactant, and lysin compound(s) capable of killing or inhibiting the growth of each bacterium listed.

| Bacteria | Infection | Lysin capable of inhibiting the growth of said bacteria |
|---|---|---|
| S. aureus | respiratory system infections, pneumonia | Also, the following Gram negative lysins identified by the present inventors:<br>GN37 (SEQ ID NO: 6)<br>GN2 (SEQ ID NO: 7)<br>GN4 (SEQ ID NO: 8)<br>GN14 (SEQ ID NO: 9)<br>GN43 (SEQ ID NO: 10)<br>PGN4 (SEQ ID NO: 11)<br>FGN4-1 (SEQ ID NO: 12)<br>FGN4-2 (SEQ ID NO: 13)<br>FGN4-3 (SEQ ID NO: 14)<br>FGN4-4 (SEQ ID NO: 15)<br>CF-301, ClyS (SEQ ID NO: 2), lysostaphin, LysK (SEQ ID NO: 4), Sal-200 and LysGH15 (which are derivatives of LysK), PlyV12 (SEQ ID NO: 3), ClyH (Yang et al. *Antimicrob Agents Chemother*. 2014 January; 58(1): 536-542) |
| S. pneumoniae | respiratory infections, pneumonia | Cpl-1 (SEQ ID NO: 5) (including dimerized form of Cpl-1), Pal (SEQ ID NO: 16) |

The entire disclosure of all documents cited in the above table are incorporated by reference in their entirety for all purposes.

Colistin (also known as polymyxin E) belongs to the polymyxin group of antibiotics. Colistin has a narrow antibacterial spectrum and is primarily used for infections with *P. aeruginosa* and *A. baumannii*. Infections associated with *P. aeruginosa* and *A. baumanni* and lysins active against these bacteria are listed in Table 3.

TABLE 3 examples of bacteria susceptible to tobramycin treatment (in the absence of surfactant), type of infection that occurs in the presence of pulmonary surfactant, and lysin compound(s) capable of killing or inhibiting the growth of each bacteria listed.

| Bacteria | Infection | Lysin capable of inhibiting the growth of said bacteria |
|---|---|---|
| P. aeruginosa | respiratory system infections, pneumonia | Artilysins, described in one or more of the following patent applications:<br>U.S. 20140120074,<br>WO/2015/070912;<br>WO/2015/071436;<br>WO/2015/070911;<br>WO/2015/071437;<br>U.S. 20150118731 and<br>WO/2012/085259<br>In addition the following lysins identified by the present inventors can be used.<br>GN37 (SEQ ID NO: 6)<br>GN2 (SEQ ID NO: 7)<br>GN4 (SEQ ID NO: 8)<br>GN14 (SEQ ID NO: 9)<br>GN43 (SEQ ID NO: 10)<br>PGN4 (SEQ ID NO: 11)<br>FGN4-1 (SEQ ID NO: 12)<br>FGN4-2 (SEQ ID NO: 13) |
| A. baumannii | respiratory infection, pneumonia | FGN4-3 (SEQ ID NO: 14)<br>FGN4-4 (SEQ ID NO: 15)<br>PlyF307 [[GenBank: KJ740396.1] |

The entire disclosure of all documents cited in the above table are incorporated by reference in their entirety for all purposes.

Pulmonary infection due to *S. aureus* can occur among individuals either in the community or in a hospital setting. Furthermore, pulmonary infection due to *S. aureus* can develop among individuals with *S. aureus* colonization of the skin or nares. Often, the infection due to *S. aureus* occurs in the context of intubation or other respiratory tract instrumentation. *S. aureus* pneumonia can also occur following viral pneumonia or in the setting of right-sided endocarditis with pulmonary emboli.

The most common causes of bacterial lung infections in normal hosts include *Streptococcus pneumoniae, Haemophilus species, Staphylococcus aureus*, and *Mycobacterium tuberculosis*.

The primary cause of morbidity and mortality in patients with cystic fibrosis (CF) is bronchiectasis and obstructive lung disease. Pulmonary disease is present in 98% of patients with CF by the time they reach adulthood. Despite the great advances in the management of this disorder, the majority of the patients succumb to respiratory complications. *S aureus* is one of the pathogens most commonly found in the airways of patients with CF. Thus, in one embodiment, the present disclosure is directed to treatment of *S. aureus* pulmonary infection in subjects with CF by administering daptomycin and a lysin active against the pathogen, such as CF-301.

As stated above, the present disclosure provides methods for restoring or augmenting surfactant-inhibited antibiotic activity comprising administering a combination of a lysin, and one or more antibiotic to an organ or a tissue wherein pulmonary surfactant is present.

In one embodiment, the present disclosure provides a method of treatment of a subject afflicted with a bacterial infection of an organ or tissue in which pulmonary surfactant is present, such as the lung or more generally the respiratory tract, comprising administering to the subject a first amount of an antibiotic that is normally inhibited by pulmonary surfactant and co-administering to the subject a second amount of a lysin polypeptide wherein the first and second amounts are together effective to treat the infection (this statement does not preclude the individual components of a combination having an effect of their own). The lysin preferably targets, i.e., it is active against, the bacteria responsible for the infection. The pathogens responsible for the infection may be resistant to at least one standard of care antibiotic but must be susceptible to the antibiotic used in the combination with lysin.

In another embodiment, the present disclosure provides a method of treatment of a subject afflicted with a bacterial infection of an organ or tissue in which pulmonary surfactant is present, such as the lung or more generally the respiratory tract, comprising administering to the subject a first amount of a lysin polypeptide and co-administering to the subject a second amount of an antibiotic that is normally inhibited by pulmonary surfactant wherein the first and second amounts are together effective to treat the infection (this statement does not preclude the individual components of a combination having an effect of their own).

In another embodiment, the infection of the airway is a staphylococcal related disease or condition (e.g., a disease or condition associated with presence of Staphylococcus bacteria including those diseases resulting from Staphylococcus infection or Staphylococcus infection is sequela to another disease or condition, such as a transplant or cancer or cancer therapy such as chemotherapy).

In some embodiments, the present disclosure provides a method for restoring or augmenting bactericidal activity of an antibiotic in a subject afflicted with a bacterial infection of an organ or tissue in which pulmonary surfactant is present in an amount that is or would be inhibitory of the activity of the antibiotic against a bacterial infection in said subject, the method comprising: administering to a subject afflicted with an infection of said organ or tissue a first amount of said antibiotic and co-administering to the subject a second amount of a lysin polypeptide having antibacterial activity against the bacterium responsible for the infection, the amounts in combination being effective to kill said bacterium and thereby treat the infection.

The present disclosure further provides methods for restoring or augmenting lysin activity, such as CF-301, comprising administering a combination of antibiotic and lysin (e.g., DAP and CF-301 lysin). In an aspect thereof, the activity of lysin CF-301 lysin is enhanced at least 2 fold, at least 4 fold, at least 8 fold, at least 10 fold, up to 10 fold, up to 16 fold, up to 20 fold, or more.

EXAMPLES

Example 1

CF-301, but not DAP, is Active in Pulmonary Surfactant

In order to determine individual activity of CF-301 and DAP against different strains of Staphylococcus aureus in the presence of surfactant, the inventors tested 3 different S. aureus strains and used bovine-derived surfactant (Survanta, AbbVie Inc), which is a functional equivalent of human surfactant. Minimum inhibitory concentration (MIC) determination was preformed using methicillin resistant strain (MRSA) MW2 (FIG. 1A), methicillin-susceptible (MSSA) strain ATCC 29213 (FIG. 1B), and vancomycin-intermediate Staphylococcus aureus (VISA) strain ATCC 700699 (FIG. 1C), in the presence of increasing concentrations of surfactant (FIG. 1). MIC values were determined by broth microdilution according to Clinical and Laboratory Standards Institute. M07-A9. Methods for dilution antimicrobial susceptibility tests for bacteria that grow aerobically; approved standard. 8th ed. Wayne, Pa.: CLSI, 2012. Briefly, each strain of bacteria was suspended in growth media using calcium-adjusted Mueller-Hinton broth at the concentration of $5 \times 10^5$ colony-forming units [CFU]/mL and exposed to CF-301 or DAP in a series of 2-fold serial dilutions in 96-well polypropylene microtiter plates (Becton, Dickinson, and Company). Following 24 hours of incubation at 35° C. in ambient air, MIC values were recorded as the most dilute concentration of each compound (CF-301 or DAP) that inhibited bacterial growth of each strain (Schuch et al, *J Infect Dis.;* 209(9):1469-78 (2014)). Starting MIC values (i.e., without surfactant) for CF-301 and DAP (respectively) were 32 and 1 µg/ml for MW2 (FIG. 1A), 16 and 1 µg/ml for ATCC 29213 (FIG. 1B) and 64 and 2 µg/ml for ATCC 700699 (FIG. 1C).

As shown in FIG. 1A-C, CF-301, but not DAP, showed antimicrobial activity in the presence of pulmonary surfactant in each strain tested. CF-301 MIC increased up to 2-fold (for a MRSA and MSSA strain) and 4-fold (for VISA) over a range of surfactant concentrations from 1.25-15% (FIG. 1A-C). DAP MIC however, increased 256-fold over the same range of surfactant as the range used for CF-301 study. Collectively, these results show that CF-301 active in the presence of surfactant against MRSA, MSSA, and VISA strains of *S. aureus*, while DAP is not active.

Example 2

DAP Activity in Pulmonary Surfactant is Permitted when Used in Combination with CF Following the findings that DAP is not active in the presence of surfactant, the inventors sought to evaluate the possibility that CF-301 promotes DAP activity in the presence of surfactant and allows DAP to excerpt its antimicrobial function even in the presence of a pulmonary surfactant. Antimicrobial activity of CF-301 and DAP together in the presence of surfactant was assessed using 2 different methods: combination MIC assay and the checkerboard assay. The checkerboard dilution test is widely used method for testing of in vitro synergy between multiple compounds (White et al. *Antimicrob Agents Chemother.* 40(8):1914-8 (1996)). Checkerboards were generated using combinations of sub-MIC CF-301 with sub-MIC daptomycin against a panel of 20 MRSA and 20 MSSA strains in 7.5% surfactant. Combination MIC assay is a variation of the microdilution method, whereby two compounds in combination (rather than a single compound) are diluted two-fold across the x-axis of a 96 well plate (Schuch et al, *J Infect Dis.;* 209(9):1469-78 (2014)) and the lowest concentration of the compound combination (in this instance CF-301 and DAP) required to inhibit growth of bacteria is determined. For purpose of experimental design, synergy was defined as inhibitory activity greater than what would be predicted by adding the 2 compounds together (ie, minimum fractional inhibitory concentration [FICmin]≤0.5) (Moody J. 2007. Synergism testing: broth microdilution checkerboard and broth macrodilution methods, p 1-23 In Garcia L S, Isenberg H D, editors. (ed), Clinical microbiology procedures handbook, 2nd ed. ASM Press, Washington, D.C.).

As shown in Table 4, combining CF-301 and DAP in the presence of 7.5% surfactant resulted in growth inhibitory concentrations 16-32-fold and 512-1024-fold lower, respectively, than when each compound was used as single agent. Importantly, combining CF-301 and DAP restored the activity of DAP despite the presence of a surfactant, indicating that the addition of lysin to otherwise surfactant-inhibited antibiotic overcomes the inhibition of such antibiotics. The results were consistent among various strains, including 5 strains of MRSA (MW2, BAA-1720, NRS-192, NRS-265, NRS-255) and 5 strains of MSSA (ATCC-29213, NRS-131, ATCC 25923, ATCC 49521, and Newman) (Table 4, data are MIC values for each drug alone and in combination.)).

Furthermore, as evident by the checkerboard assay using MHB supplemented with 7.5% surfactant, sub-MIC concentrations of CF-301 and DAP exhibited potent synergy (FIC≤0.5) against a panel of 20 MRSA and MSSA strains (Tables 5 and 6). For values listed in Tables 2 and 3, individual MICs and combination fractional inhibitory concentrations (FICs) are shown, wherein FIC values≤0.5 indicate strong synergy.

Taken together, these results demonstrate that CF-301 restores and promotes DAP activity in the presence of pulmonary surfactant.

TABLE 4

Combining CF-301 and DAP restores DAP activity on the presence of surfactant and CF-301 and DAP are highly active together against S. aureus in 7.5% surfactant.

| | | CF-301 | | | Daptomycin | | |
|---|---|---|---|---|---|---|---|
| | Strain | MIC alone | MIC combo | Fold reduction | MIC alone | MIC combo | Fold reduction |
| MRSA | MW2 | 64 | 2 | 32 | 256 | 0.25 | 1024 |
| | BAA-1720 | 64 | 2 | 32 | 256 | 0.25 | 1024 |
| | NRS-192 | 64 | 4 | 16 | 256 | 0.5 | 512 |
| | NRS-265 | 64 | 4 | 16 | 256 | 0.25 | 1024 |
| | NRS-255 | 64 | 2 | 16 | 512 | 0.5 | 1024 |
| MSSA | ATCC 29213 | 128 | 4 | 32 | 256 | 0.5 | 512 |
| | NRS-131 | 64 | 4 | 16 | 512 | 0.5 | 1024 |
| | ATCC 25923 | 128 | 4 | 32 | 256 | 0.5 | 512 |
| | ATCC 49521 | 64 | 2 | 32 | 256 | 0.5 | 512 |
| | Newman | 128 | 4 | 32 | 256 | 0.5 | 512 |

TABLE 5

CF-301 synergizes with DAP against MRSA isolates in 7.5% surfactant.

| CFS# (strain name) | CF-301 MIC | DAP MIC | FIC |
|---|---|---|---|
| 269 (MW2) | 64 | 256 | 0.375 |
| 223 (BAA-1720) | 64 | 256 | 0.375 |
| 738 (NRS-192) | 64 | 256 | 0.312 |
| 735 (NRS-265) | 64 | 256 | 0.500 |
| 743 (NRS-255) | 64 | 256 | 0.375 |
| 218 (BAA-42) | 64 | 256 | 0.375 |
| 836 (BAA-1688) | 128 | 256 | 0.312 |
| 958 (JMI-227) | 128 | 256 | 0.375 |
| 962 (JMI-1004)* | 64 | 256 | 0.500 |
| 981 (JMI-3346)* | 64 | 256 | 0.312 |

*Respiratory isolate

TABLE 6

CF-301 synergizes with DAP against MSSA isolates in 7.5% surfactant.

| CFS# (strain name) | CF-301 MIC | DAP MIC | FIC |
|---|---|---|---|
| 554 (ATCC 25923) | 128 | 256 | 0.5 |
| 581 (ATCC 29213) | 128 | 256 | 0.5 |
| 919 (ATCC 49521) | 64 | 256 | 0.5 |
| 28 (Newman) | 128 | 256 | 0.5 |
| 258 (NRS-153) | 128 | 256 | 0.5 |
| 766 (NRS-106) | 64 | 256 | 0.375 |
| 757 (NRS-131) | 64 | 256 | 0.375 |
| 960 (JMI-316)* | 128 | 256 | 0.312 |
| 964 (JMI-1040)* | 128 | 256 | 0.5 |
| 966 (JMI-1173)* | 128 | 256 | 0.375 |

*Respiratory isolate

Example 3

Cf-301 Promotes (or Allows) Dap Binding to Staphylococcus Aureus

Given that CF-301 restores the activity of DAP in the presence of surfactant (Example 2), the inventors postulated that CF-301 promotes DAP binding to Staphylococcus aureus. BODIPY-labeled daptomycin (BDP-DAP) assay was used to assess the interaction of DAP with the bacterial cell membrane (CM), as described before (Tran et al. MBio.,23; 4(4) (2013)). Briefly, mid-log phase MRSA MW2 (FIG. 2) and VISA ATCC 700699 (FIG. 3) strain cells were stained with DAPI, washed, and resuspended in 25mM Tris pH 7.2 with 50 µg/ml $CaCl_2$ and 7.5% surfactant. The BODIPY-DAP was then added (to 4 µg/ml), followed by CF-301 (to 4 or 8 µg/ml). A control contained no CF-301. After incubation for either 30 or 60 minutes at room temperature, cells were diluted, washed, fixed and plated on 0.01% lysine coated slides before visualization by fluorescence microscopy (FIG. 2, 1000×; FIG. 3, Mag=2000×).

Figure 2:
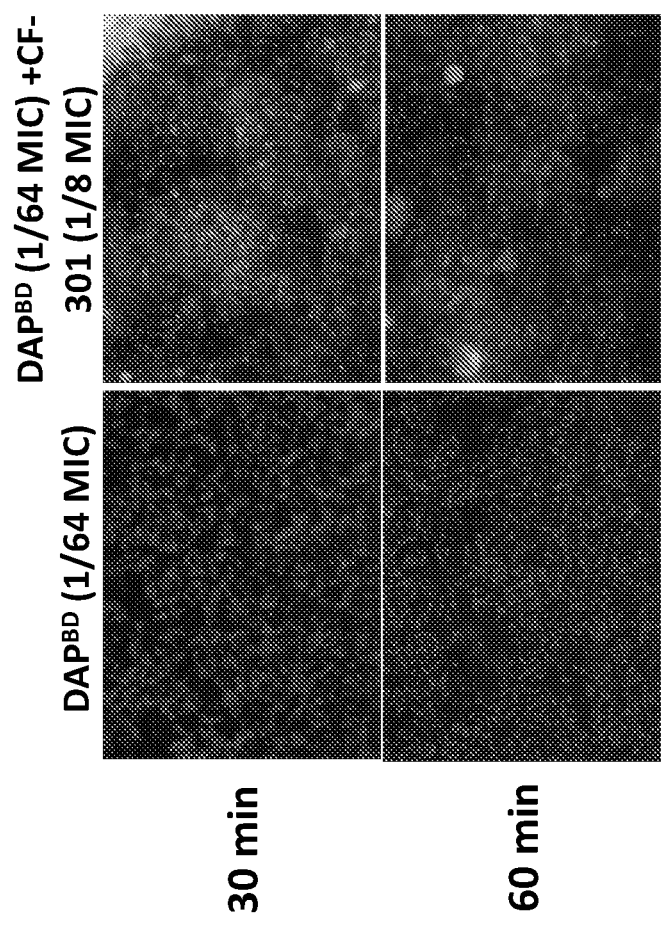
FIG. 2 includes images demonstrating that CF-301 promotes BODIPY-DAP ($DAP^{BD}$) binding to MRSA in 7.5% surfactant. Mag:1000×.
Figure 3:
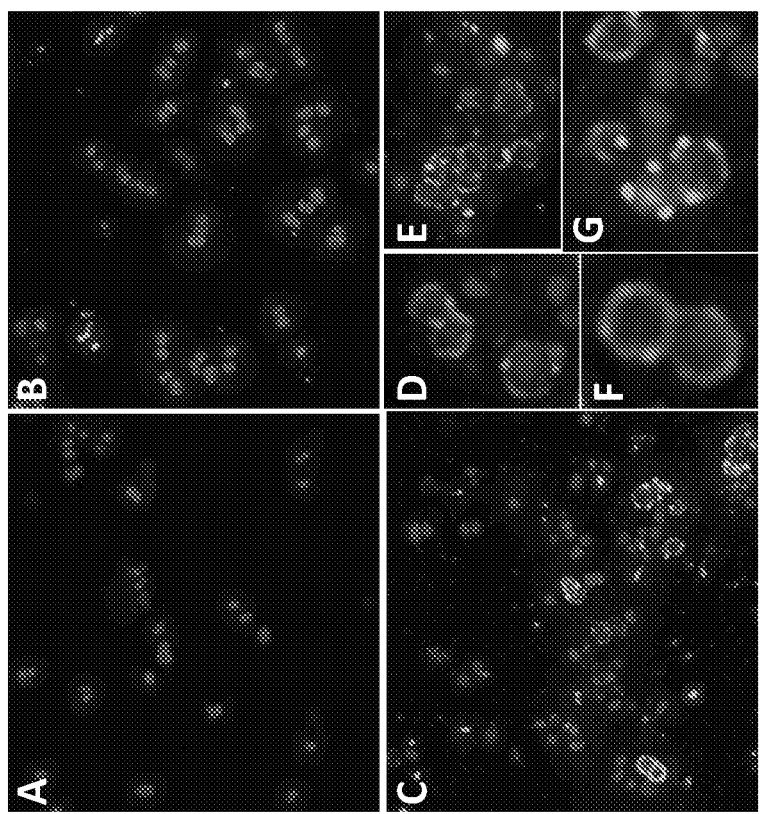
FIG. 3 includes images demonstrating that CF-301 promotes $DAP^{BD}$ binding to VISA in 7.5% surfactant. Mag=2000×.

As shown in FIG. 2, CF-301 (8 µg/ml) promoted BODIPY-DAP ($DAP^{BD}$) binding to MRSA in the presence of 7.5% surfactant. Similarly, CF-301 (4 µg/m) promoted $DAP^{BD}$ binding to VISA in 7.5% surfactant (FIG. 3, VISA strain ATCC 700699 labeled with DAPI and treated 30 min with buffer (FIG. 3A), $DAP^{BD}$ (4 µg/ml; 1/64 MIC) (FIG. 3B), or $DAP^{BD}$ and CF-301 (4 µg/ml; 1/128 MIC) (FIGS. 3C-G).). Collectively, these findings indicate that CF-301 promotes DAP binding to bacterial CM.

Example 4

Figure 4:
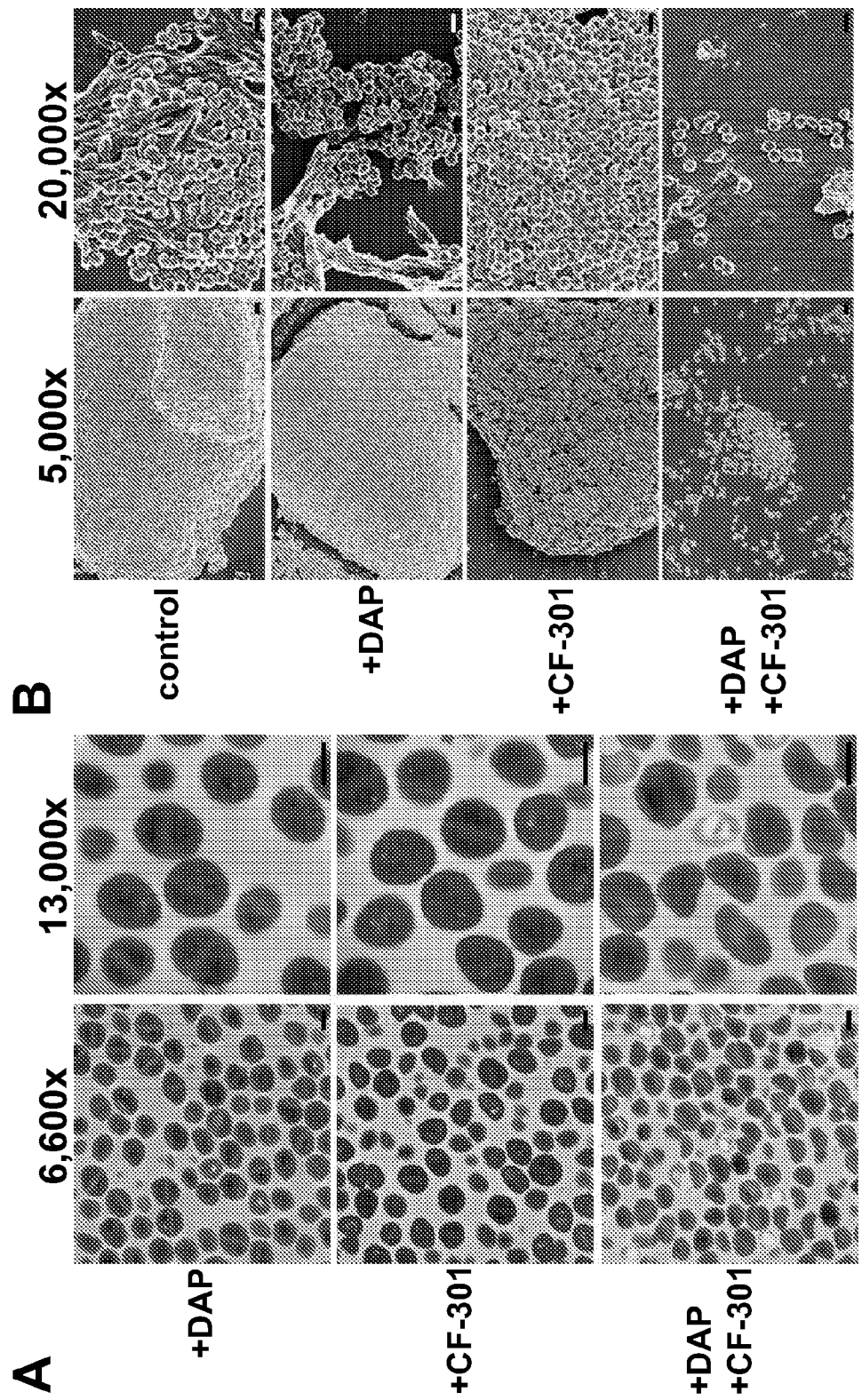
FIG. 4 includes TEM (FIG. 4A) and SEM (FIG. 4B) analysis images demonstrating that CF-301 and DAP act together to kill S. aureus and reduce biofilm-like structures in 7.5% surfactant.

CF-301 and DAP Act Together to Kill S. aureus and Reduce/Disrupt Biofilm-Like Structures in 7.5% Surfactant Next, the inventors investigated the ability of CF-301 and DAP together to kill S. aureus and reduce and disrupt the biofilm-like structures in the presence of surfactant in 25 mM Tris pH7.2 (with 50 µg/ml $CaCl_2$ and 7.5% surfactant). VISA strain ATCC 700699 was treated for 20 min alone (control) or with DAP (4 µg/ml; 1/64 MIC), CF-301 (4 µg/ml; 1/128 MIC), or the combination of DAP and CF-301 Transmission electron microscopy (TEM) (FIG. 4A) and scanning electron microscopy (SEM) (FIG. 4B) analysis indicate the efficient killing of S. aureus (FIG. 4A), as well as the reduction in biofilm formation (FIG. 4B) when CF-301 and DAP were combined. Thus, similarly to what was observed in prior examples, these observations indicate that CF-301 allows DAP to overcome inhibitory effects of surfactant.

Example 5

Combination Therapy with CF-301 and DAP is Superior to Monotherapy in a Murine Model of S. aureus Pneumonia Considering the advantages observed in vitro when CF-301 and DAP were combined, the effects of using CF-301 and DAP together in vivo were evaluated. In order to address this question, mice were infected intranasally with $5×10^8$CFUs of S. aureus (MRSA strain ATCC BAA-42) and treated with saline, CF-301 (i.v.), DAP (s.c.), or the CF-301/DAP combination once daily beginning four hours after the start of infection (n=10 mice/group; p<0.05 vs. DAP). The experiment was carried out for 14 days post infection. At 14 days, treatment with the CF-301 and DAP combination resulted in 70% survival, demonstrating that combination therapy was superior to either drug alone (P<0.05 vs. DAP).

Figure 5:
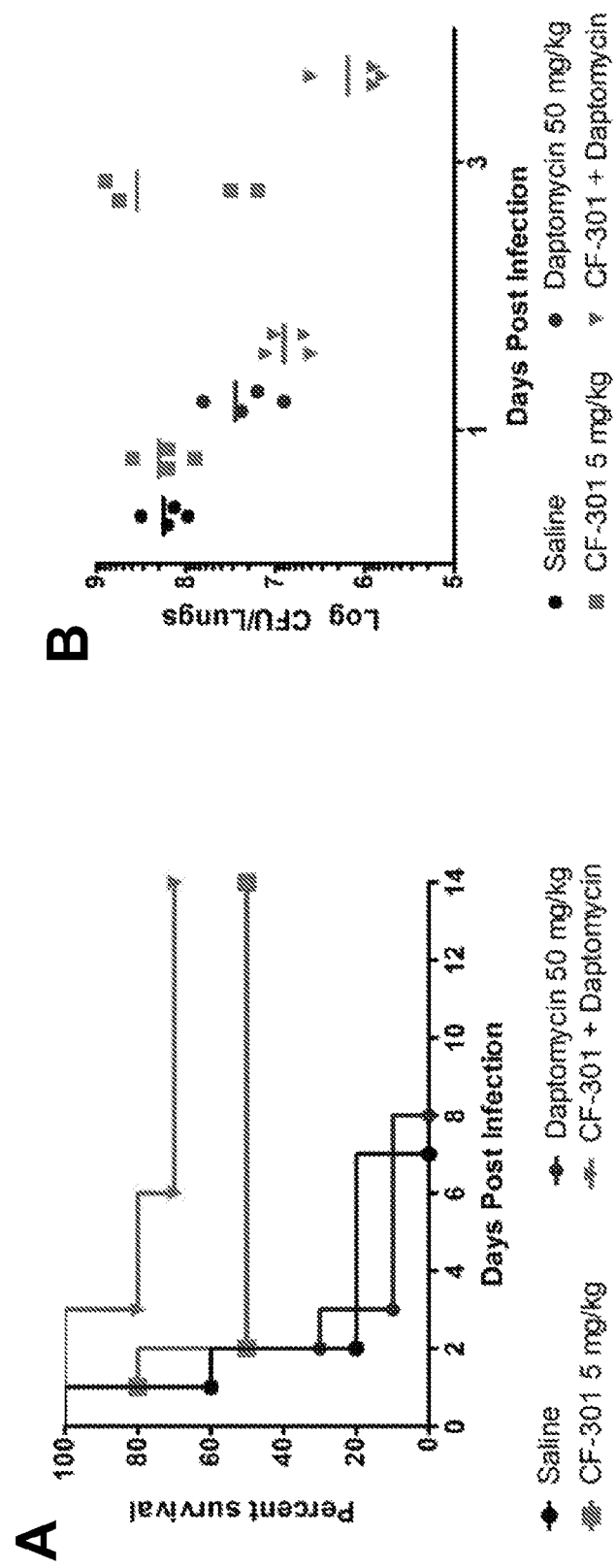
FIG. 5A is a survival curve of mice infected intranasally with $5 \times 10^8$ CPUs of S. aureus (MRSA strain ATCC BAA-42) and treated with saline, CF-301 (i.v.), DAP (s.c.), or the CF-301/DAP. (n=10 mice/group; p<0.05 vs. DAP).
FIG. 5B is a plot of Log of CFU/lungs 1 and 3 days post infection.

As shown in FIG. 5A, combination therapy with CF-301 and DAP was superior to monotherapy in a murine model of *S. aureus* pneumonia. Similar to what was observed in vitro, use of CF-301 in addition to DAP results in the restoration of DAP antimicrobial activity. In vivo data obtained here further supports those findings. For example, animals treated with DAP alone exhibit same survival pattern as those treated with saline (control). However, addition of CF-301 to DAP treatment restores the antimicrobial activity of CF-301.

Furthermore, the total number of bacterial CFUs in the lungs of each of 4 infected animals groups (measured 1 and 3 days post infection) was significantly reduced after the treatment with CF-301 and DAP combined (FIG. 5B).

As shown by the Examples described herein, CF-301 promotes DAP activity and permits its antimicrobial effects to be carried out in the presence of surfactant. These findings were corroborated both in vitro and in vivo.

In summary, the inventors have used minimum (and in some experiments sub-minimum) inhibitory concentration (MIC) and checkerboard assays with and without bovine pulmonary surfactant (functional equivalent of human surfactant), to show a potent synergistic interaction between CF-301 and DAP against MRSA. MSSA, and VISA *Staphylococcus aureus* isolates. MIC reductions of up to 1024-fold were observed for DAP in the presence of CF-301 in surfactant. Furthermore, efficacy of CF-301 and/or DAP was demonstrated in a BALB/c mouse lung infection model following survival and CFU levels. The in vitro and in vivo results shown in Examples 1-5 suggest that CF-301 combination with DAP could be an effective therapy targeting *S. aureus* lung infections.

CF-301 synergizes with DAP—at sub-MIC levels—to kill a range of MSSA and MRSA isolates in the presence of pulmonary surfactant (a potent inhibitor of DAP). The results show a more rapid accumulation of DAP within bacterial cells in the presence of CF-301. Significantly, the combination therapy is highly efficacious in the lung environment of infected mice, suggesting that CF-301 and DAP is effective at treating staphylococcal pneumonia, a new indication for both drugs. The complementary and synergistic activities of these agents are reinforced by the novel features of CF-301, which includes rapid bacteriolysis, specificity for *S. aureus*, the absence of resistance, and potent anti-biofilm activity.

All references cited herein are incorporated by reference in their entirety for all purposes. The foregoing examples are illustrative and nonlimiting. While specific embodiments are described above, those of skill in the art will readily be able to envision additional embodiments, modifications and variations all within the scope of the claims set forth below including equivalents.

```
(CF-301, GenBank Accession Number: ZP_03625529)
                                                   Sequence ID NO: 1
ATGACAACAG TAAATGAAGC ATTAAATAAT GTAAGAGCTC AGGTTGGGTC

CGGTGTGTCT GTTGGCAACG GCGAATGCTA CGCTTTGGCT AGTTGGTACG

AGCGCATGAT TAGTCCGGAT GCAACTGTCG GACTTGGCGC TGGTGTGGGC

TGGGTCAGCG GTGCAATCGG CGATACAATC TCTGCCAAAA ACATCGGCTC

ATCATACAAC TGGCAAGCTA ACGGCTGGAC AGTTTCCACA TCTGGGCCAT

TTAAAGCAGG TCAGATTGTG ACGCTTGGGG CAACACCAGG AAACCCTTAC

GGACATGTGG TAATCGTCGA AGCAGTGGAC GGCGATAGAT TGACTATTTT

GGAGCAAAAC TACGGCGGGA AACGTTATCC CGTCCGTAAT TATTACAGCG

CTGCAAGCTA TCGTCAACAG GTCGTGCATT ACATCACACC GCCTGGCACG

GTCGCACAGT CAGCACCCAA CCTTGCAGGC TCTCGTTCCT ATCGCGAGAC

GGGCACTATG ACTGTCACGG TCGATGCTCT CAATGTTCGC AGGGCGCCAA

ATACTTCAGG CGAGATTGTA GCAGTATACA AGCGTGGTGA ATCATTTGAC

TATGATACTG TCATCATCGA TGTCAATGGC TATGTCTGGG TGTCTTACAT

AGGCGGCAGC GGCAAACGTA ACTACGTTGC GACGGGCGCT ACCAAAGACG

GTAAGCGTTT CGGCAATGCT TGGGGTACAT TTAAATAA (ClyS)
                                                   Sequence ID NO: 2
Met Glu Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
                20                  25                  30

Ala Val Asp Tyr Ile Tyr His Val Thr Asp Gly Lys Ile Arg Met Trp
            35                  40                  45

Gly Asn Ala Lys Asp Ala Ile Asn Asn Ser Phe Gly Gly Thr Ala Thr
        50                  55                  60
```

-continued

```
Val Tyr Lys Asn Tyr Pro Ala Phe Arg Pro Lys Tyr Gly Asp Val Val
 65                  70                  75                  80

Val Trp Thr Thr Gly Asn Phe Ala Thr Tyr Gly His Ile Ala Ile Val
                 85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile Arg Pro Asn Phe
    130                 135                 140

Ala Thr Glu Ser Ser Val Lys Lys Asp Thr Lys Lys Lys Pro Lys
145                 150                 155                 160

Pro Ser Asn Arg Asp Gly Ile Asn Lys Asp Lys Ile Val Tyr Asp Arg
                165                 170                 175

Thr Asn Ile Asn Tyr Asn Met Val Leu Gln Gly Lys Ser Ala Ser Lys
            180                 185                 190

Ile Thr Val Gly Ser Lys Ala Pro Tyr Asn Leu Lys Trp Ser Lys Gly
        195                 200                 205

Ala Tyr Phe Asn Ala Lys Ile Asp Gly Leu Gly Ala Thr Ser Ala Thr
    210                 215                 220

Arg Tyr Gly Asp Asn Arg Thr Asn Tyr Arg Phe Asp Val Gly Gln Ala
225                 230                 235                 240

Val Tyr Ala Pro Gly Thr Leu Ile Tyr Val Phe Glu Ile Ile Asp Gly
                245                 250                 255

Trp Cys Arg Ile Tyr Trp Asn Asn His Asn Glu Trp Ile Trp His Glu
            260                 265                 270

Arg Leu Ile Val Lys Glu Val Phe
        275
```

(PlyV12)

SEQ ID NO: 3

MTRRYTKMNVPQSLVNWFVNHRNLLTYSMYGSRNGSDGTADCSGSMSQAL

KEAGIPIQGLPSTVTLGQQLAKNGFYR

ISRNEDWNAETGDIVLMSWGADMASSGGAGGHVGVMMDSVNFISCDYSTQ

GAAGQAINTYPWNDYYEANKPAYIEVW

RYSESAPQTKNQANTAVTPQQKAYYEANEVKYVNGIWQIKCDYLSPIGFDYL

ENGIPVTMVNWVDKDGNDLPDGADQ

DLKAGMYFSFSSDETNIVDTGNGGYYGGYYWRLFEFGQFGPVWLSCWNKD

DLVNYFQ (LysK)

SEQ ID NO: 4

MAKTQAEINK RLDAYAKGTV DSPYRVKKAT SYDPSFGVME

AGAIDADGYY

HAQCQDLITD YVLWLTDNKV RTWGNAKDQI KQSYGTGFKI HENKPSTVPK

KGWIAVFTSG SYEQWGHIGI VYDGGNTSTF TILEQNWNGY ANKKPTKRVD

NYYGLTHFIE IPVKAGTTVK KKTAKKSASK TPAPKKKATL KVSKNHINYT

MDKRGKKPEG MVIHNDAGRS SGQQYENSLA NAGYARYANG

IAHYYGSEGY

VWEAIDAKNQ IAWHTGDGTG ANSGNFRFAG IEVCQSMSAS DAQFLKNEQA

VFQFTAEKFK EWGLTPNRKT VRLHMEFVPT ACPHRSMVLH TGFNPVTQGR

-continued

PSQAIMNKLK DYFIKQIKNY MDKGTSSSTV VKDGKTSSAS TPATRPVTGS

WKKNQYGTWY KPENATFVNG NQPIVTRIGS PFLNAPVGGN LPAGATIVYD

EVCIQAGHIW IGYNAYNGNR VYCPVRTCQG VPPNQIPGVA WGVFK (Cp1-1)
SEQ ID NO: 5
MVKKNDLFVD VSSHNGYDIT GILEQMGTTN TIIKISESTT

YLNPCLSAQVEQSNPIGFYH FARFGGDVAE AEREAQFFLD NVPMQVKYLV

LDYEDDPSGD AQANTNACLR FMQMIADAGYKPIYYSYKPF THDNVDYQQI

LAQFPNSLWI AGYGLNDGTA NFEYFPSMDG IRWWQYSSNP

FDKNIVLLDDEEDDKPKTAG TWKQDSKGWW FRRNNGSFPY

NKWEKIGGVW YYFDSKGYCL TSEWLKDNEK

WYYLKDNGAMATGWVLVGSE WYYMDDSGAM VTGWVKYKNN

WYYMTNERGN MVSNEFIKSG KGWYFMNTNG ELADNPSFTKEPDGLITVA

GN37
Polypeptide sequence
SEQ ID NO: 6
MTYTLSKRSLDNLKGVHPDLVAVVHRAIQLTPVDFAVIEGLRSVSRQKEL

VAAGASKTMNSRHLTGHAVDLAAYVNGIRWDWPLYDAIAVAVKAAAKELG

VAIVWGGDWTTFKDGPHFELDRSKYR

GN2
Polypeptide sequence
SEQ ID NO: 7
MKISLEGLSLIKKFEGCKLEAYKCSAGVWTIGYGHTAGVKEGDVCTQEEAEK

LLRGDIFKFEEYVQDSVKVDLDQSQFDALVAWTFNLGPGNLRSSTMLKKLNN

GEYESVPFEMRRWNKAGGKTLDGLIRRRQAESLLFESKEWHQV

GN4
Polypeptide sequence
SEQ ID NO: 8
MRTSQRGIDLIKSFEGLRLSAYQDSVGVWTIGYGTTRGVTRYMTITVEQAER

MLSNDIQRFEPELDRLAKVPLNQNQWDALMSFVYNLGAANLASSTLLKLLN

KGDYQGAADQFPRWVNAGGKRLDGLVKRRAAERALFLEPLS

GN14
Polypeptide sequence
SEQ ID NO: 9
MNNELPWVAEARKYIGLREDTSKTSHNPKLLAMLDRMGEFSNESRAWWHD

DETPWCGLFVGYCLGVAGRYVVREWYRARAWEAPQLTKLDRPAYGALVTF

TRSGGGHVGFIVGKDARGNLMVLGGNQSNAVSIAPFAVSRVTGYFWPSFWR

NKTAVKSVPFEERYSLPLLKSNGELSTNEA

GN43
Polypeptide sequence
SEQ ID NO: 10
MKRTTLNLELESNTDRLLQEKDDLLPQSVTNSSDEGTPFAQVEGASDDNTAE

QDSDKPGASVADADTKPVDPEWKTITVASGDTLSTVFTKAGLSTSAMHDML

TSSKDAKRFTHLKVGQEVKLKLDPKGELQALRVKQSELETIGLDKTDKGYSF

KREKAQIDLHTAYAHGRITSSLFVAGRNAGLPYNLVTSLSNIFGYDIDFALDL

REGDEFDVIYEQHKVNGKQVATGNILAARFVNRGKTYTAVRYTNKQGNTSY

-continued

```
YRADGSSMRKAFIRTPVDFARISSRFSLGRRHPILNKIRAHKGVDYAAPIGTPI

KATGDGKILEAGRKGGYGNAVVIQHGQRYRTIYGHMSRFAKGIRAGTSVKQ

GQIIGYVGMTGLATGPHLHYEFQINGRHVDPLSAKLPMADPLGGADRKRFM

AQTQPMIARMDQEKKTLLALNKQR

PGN4
Polypeptide sequence
                                                      SEQ ID NO: 11
NKGDYQGAADQFPRWVNAGGKRLDGLVKRRASQSRESQC FGN4-1
Polypeptide Sequence
                                                      SEQ ID NO: 12
NKGDYQGAADQFPRWVNAGGKRLDGLVKRRAAERALFLEPLS FGN4-2
Polypeptide Sequence
                                                      SEQ ID NO: 13
NKGDYQGAADQFPRWVNAGGKRLDGLVKRRA FGN4-3
Polypeptide sequence
                                                      SEQ ID NO: 14
NKGDYQGAADQFPRWVNAGGKRLDGLVKRRK Polypeptide sequence
                                                      SEQ ID NO: 15
NKGDYQGAADQFPRWVNAGGKRLDGLVKRRAAERALFLEPLSC
```

Sequence ID 16: PAL Sequence

| | | | | | | | | | | | | | | |
|---|---|---|---|---|---|---|---|---|---|---|---|---|---|---|
| Met | Ala | Lys | Thr | Gln | Ala | Glu | Ile | Asn | Lys | Arg | Leu | Asp | Ala | Tyr | Ala |
| 1 | | | | 5 | | | | | 10 | | | | | 15 | |
| Lys | Gly | Thr | val | Asp | Ser | Pro | Tyr | Arg | val | Lys | Lys | Ala | Thr | Ser | Tyr |
| | | | 20 | | | | | 25 | | | | | 30 | | |
| Asp | Pro | Ser | Phe | Gly | Val | Met | Glu | Ala | Gly | Ala | Ile | Asp | Ala | Asp | Gly |
| | | | 35 | | | | | 40 | | | | | 45 | | |
| Tyr | Tyr | His | Ala | Gln | cys | Gln | Asp | Leu | Ile | Thr | Asp | Tyr | Val | Leu | Trp |
| | | | 50 | | | | | 55 | | | | | 60 | | |
| Leu | Thr | Asp | Asn | Lys | val | Arg | Thr | Trp | Gly | Asn | Ala | Lys | Asp | Gln | Ile |
| 65 | | | | | 70 | | | | | 75 | | | | | 80 |
| Lys | Gln | Ser | Tyr | Gly | Thr | Gly | Phe | Lys | Ile | His | Glu | Asn | Lys | Pro | Ser |
| | | | | 85 | | | | | 90 | | | | | 95 | |
| Thr | val | Pro | Lys | Lys | Gly | Trp | Ile | Ala | Val | Phe | Thr | Ser | Gly | Ser | Tyr |
| | | | | 100 | | | | | 105 | | | | | 110 | |
| Glu | Gln | Trp | Gly | His | Ile | Gly | Ile | Val | Tyr | Asp | Gly | Gly | Asn | Thr | Ser |
| | | | 115 | | | | | 120 | | | | | 125 | | |
| Thr | Phe | Thr | Ile | Leu | Glu | Gln | Asn | Trp | Asn | Gly | Tyr | Ala | Asn | Lys | Lys |
| | | | 130 | | | | | 135 | | | | | 140 | | |
| Pro | Thr | Lys | Arg | Val | Asp | Asn | Tyr | Tyr | Gly | Leu | Thr | His | Phe | Ile | Glu |
| 145 | | | | | 150 | | | | | 155 | | | | | 160 |
| Ile | Pro | val | Lys | Ala | Gly | Thr | Thr | Val | Lys | Lys | Glu | Thr | Ala | Lys | Lys |
| | | | | 165 | | | | | 170 | | | | | 175 | |
| Ser | Ala | Ser | Lys | Thr | Pro | Ala | Pro | Lys | Lys | Lys | Ala | Thr | Leu | Lys | Val |
| | | | | 180 | | | | | 185 | | | | | 190 | |
| Ser | Lys | Asn | His | Ile | Asn | Tyr | Thr | Met | Asp | Lys | Arg | Gly | Lys | Lys | Pro |
| | | | 195 | | | | | 200 | | | | | 205 | | |
| Glu | Gly | Met | Val | Ile | His | Asn | Asp | Ala | Gly | Arg | Ser | Ser | Gly | Gln | Gln |
| | | | 210 | | | | | 215 | | | | | 220 | | |
| Tyr | Glu | Asn | Ser | Leu | Ala | Asn | Ala | Gly | Tyr | Ala | Arg | Tyr | Ala | Asn | Gly |
| 225 | | | | | 230 | | | | | 235 | | | | | 240 |
| Ile | Ala | His | Tyr | Tyr | Gly | Ser | Glu | Gly | Tyr | val | Trp | Glu | Ala | Ile | Asp |

```
        245                 250                 255
Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
        275                 280                 285

Ala Ser Asp Ala Gln Phe Leu Lys Asn Glu Gln Ala Val Phe Gln Phe
    290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
        355                 360                 365

Asn Tyr Met Asp Lys Gly Thr Ser Ser Ser Thr Val Val Lys Asp Gly
    370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
                405                 410                 415

Phe val Asn Gly Asn Gln Pro Ile Val Thr Arg Ile Gly Ser Pro Phe
            420                 425                 430

Leu Asn Ala Pro Val Gly Gly Asn Leu Pro Ala Gly Ala Thr Ile Val
        435                 440                 445

Tyr Asp Glu Val Cys Ile Gln Ala Gly His Ile Trp Ile Gly Tyr Asn
    450                 455                 460

Ala Tyr Asn Gly Asn Arg Val Tyr Cys Pro Val Arg Thr Cys Gln Gly
465                 470                 475                 480

Val Pro Pro Asn Gln Ile Pro Gly Val Ala Trp Gly Val Phe Lys
                485                 490                 495
```

---

What is claimed is:

1. A method for treating a subject afflicted with a Gram-negative bacterial infection of respiratory tract tissue in which pulmonary surfactant is present, the method comprising regardless of order the following steps:
   a. administering to the subject a first amount of an antibiotic having antibacterial activity against the Gram-negative bacteria responsible for the infection which activity is inhibited by the pulmonary surfactant;
   b. co-administering to the subject a second amount of a lysin polypeptide, wherein said lysin polypeptide does not require an exogenously-derived cationic peptide to have activity against the Gram-negative bacteria responsible for the infection;
   wherein said first and second amount in combination are effective to kill the Gram-negative bacteria responsible for the infection and thereby treat the infection in the respiratory tract tissue; and
   wherein the lysin polypeptide is selected from the group consisting of Gram-negative lysin polypeptides having the sequences SEQ ID NO: 8 (GN4); SEQ ID NO: 12 (FGN4-1); SEQ ID NO: 13 (FGN4-2); SEQ ID NO: 14 (FGN4-3); and SEQ ID NO: 15 (FGN4-4).

2. The method of claim 1 wherein the first amount would be ineffective to treat the infection if the antibiotic were administered as monotherapy.

3. The method of claim 1 wherein the antibiotic is a cyclic lipopeptide or an aminoglycoside.

4. The method of claim 2 wherein the antibiotic is a cyclic lipopeptide.

5. The method of claim 2 wherein the antibiotic is tobramycin.

6. The method of claim 1 wherein the second amount is a subthreshold amount.

7. The method of claim 1 wherein the first amount is a subthreshold amount.

8. The method of claim 1 wherein said lysin polypeptide is administered parenterally or by inhalation.

9. The method of claim 1 wherein said antibiotic is administered orally or parenterally or by inhalation.

10. The method of claim 1 wherein said subject is a mammalian subject.

11. The method of claim 1 wherein the Gram-negative bacteria is *Pseudomonas aeruginosa.*

12. The method of claim 1 wherein the antibiotic is colistin.

13. The method of claim 1 wherein the antibiotic is tobramycin.

14. A method for treating a subject afflicted with a Gram-negative bacterial infection of the lower respiratory tract in which pulmonary surfactant is present, which subject has already been administered an antibiotic suitable for treating the infection, the method comprising continuing administration of the antibiotic to the subject and commencing co-administration to the subject of a bactericidal activity-restoring amount of a lysin polypeptide having activity against the Gram-negative bacteria responsible for the infection in the subject and thereby restoring bactericidal activity of the antibiotic against the Gram-negative bacteria responsible for the infection of the lower respiratory tract of the subject, wherein said lysin polypeptide does not require an exogenously-derived cationic peptide to have activity against the Gram-negative bacterial responsible for the infection; and
   wherein the lysin polypeptide is selected from the group consisting of Gram-negative lysin polypeptides having the sequences SEQ ID NO: 8 (GN4); SEQ ID NO: 12 (GN04-1); SEQ ID NO: 13 (FGN4-2); SEQ ID NO: 14 (FGN4-3); and SEQ ID NO: 15 (FNG4-4).

15. The method of claim 1, wherein the lysin polypeptide further comprises at least one heterologous peptide segment covalently linked to the lysin polypeptide.

16. The method of claim 15, wherein the at least one heterologous peptide segment is an exogenous antimicrobial peptide.

17. The method of claim 16, wherein the lysin polypeptide is SEQ ID NO: 11 (PGN4).

* * * * *

SEQUENCE LISTING

<160> NUMBER OF SEQ ID NOS: 16

<210> SEQ ID NO 1
<211> LENGTH: 738
<212> TYPE: DNA
<213> ORGANISM: Streptococcus suis

<400> SEQUENCE: 1

```
atgacaacag taaatgaagc attaaataat gtaagagctc aggttgggtc cggtgtgtct      60
gttggcaacg gcgaatgcta cgctttggct agttggtacg agcgcatgat tagtccggat     120
gcaactgtcg gacttggcgc tggtgtgggc tgggtcagcg gtgcaatcgg cgatacaatc     180
tctgccaaaa acatcggctc atcatacaac tggcaagcta acggctggac agtttccaca     240
tctggtccat ttaaagcagg tcagattgtg acgcttgggg caacaccagg aaacccttac     300
ggacatgtgg taatcgtcga agcagtggac ggcgatagat tgactatttt ggagcaaaac     360
tacggcggga aacgttatcc cgtccgtaat tattacagcg ctgcaagcta tcgtcaacag     420
gtcgtgcatt acatcacacc gcctggcacg gtcgcacagt cagcacccaa ccttgcaggc     480
tctcgttcct atcgcgagac gggcactatg actgtcacgg tcgatgctct caatgttcgc     540
agggcgccaa atacttcagg cgagattgta gcagtataca agcgtggtga atcatttgac     600
```

```
tatgatactg tcatcatcga tgtcaatggc tatgtctggg tgtcttacat aggcggcagc       660
ggcaaacgta actacgttgc gacgggcgct accaaagacg gtaagcgttt cggcaatgct       720
tggggtacat ttaaataa                                                    738
```

<210> SEQ ID NO 2
<211> LENGTH: 280
<212> TYPE: PRT
<213> ORGANISM: Unknown
<220> FEATURE:
<221> NAME/KEY: source
<223> OTHER INFORMATION: /note="Description of Unknown: ClyS lysin sequence"

<400> SEQUENCE: 2

```
Met Glu Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
    50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile Arg Pro Asn Phe
    130                 135                 140

Ala Thr Glu Ser Ser Val Lys Lys Asp Thr Lys Lys Pro Lys
145                 150                 155                 160

Pro Ser Asn Arg Asp Gly Ile Asn Lys Asp Lys Ile Val Tyr Asp Arg
                165                 170                 175

Thr Asn Ile Asn Tyr Asn Met Val Leu Gln Gly Lys Ser Ala Ser Lys
            180                 185                 190

Ile Thr Val Gly Ser Lys Ala Pro Tyr Asn Leu Lys Trp Ser Lys Gly
        195                 200                 205

Ala Tyr Phe Asn Ala Lys Ile Asp Gly Leu Gly Ala Thr Ser Ala Thr
    210                 215                 220

Arg Tyr Gly Asp Asn Arg Thr Asn Tyr Arg Phe Asp Val Gly Gln Ala
225                 230                 235                 240

Val Tyr Ala Pro Gly Thr Leu Ile Tyr Val Phe Glu Ile Ile Asp Gly
                245                 250                 255

Trp Cys Arg Ile Tyr Trp Asn Asn His Asn Glu Trp Ile Trp His Glu
            260                 265                 270

Arg Leu Ile Val Lys Glu Val Phe
        275                 280
```

<210> SEQ ID NO 3
<211> LENGTH: 288
<212> TYPE: PRT
<213> ORGANISM: Unknown
<220> FEATURE:

```
<221> NAME/KEY: source
<223> OTHER INFORMATION: /note="Description of Unknown:
      PlyV12 lysin sequence"

<400> SEQUENCE: 3
```

Met Thr Arg Arg Tyr Thr Lys Met Asn Val Pro Gln Ser Leu Val Asn
1               5                   10                  15

Trp Phe Val Asn His Arg Asn Leu Leu Thr Tyr Ser Met Tyr Gly Ser
            20                  25                  30

Arg Asn Gly Ser Asp Gly Thr Ala Asp Cys Ser Gly Ser Met Ser Gln
        35                  40                  45

Ala Leu Lys Glu Ala Gly Ile Pro Ile Gln Gly Leu Pro Ser Thr Val
50                  55                  60

Thr Leu Gly Gln Gln Leu Ala Lys Asn Gly Phe Tyr Arg Ile Ser Arg
65                  70                  75                  80

Asn Glu Asp Trp Asn Ala Glu Thr Gly Asp Ile Val Leu Met Ser Trp
                85                  90                  95

Gly Ala Asp Met Ala Ser Ser Gly Gly Ala Gly His Val Gly Val
                100                 105                 110

Met Met Asp Ser Val Asn Phe Ile Ser Cys Asp Tyr Ser Thr Gln Gly
            115                 120                 125

Ala Ala Gly Gln Ala Ile Asn Thr Tyr Pro Trp Asn Asp Tyr Tyr Glu
        130                 135                 140

Ala Asn Lys Pro Ala Tyr Ile Glu Val Trp Arg Tyr Ser Glu Ser Ala
145                 150                 155                 160

Pro Gln Thr Lys Asn Gln Ala Asn Thr Ala Val Thr Pro Gln Gln Lys
                165                 170                 175

Ala Tyr Tyr Glu Ala Asn Glu Val Lys Tyr Val Asn Gly Ile Trp Gln
            180                 185                 190

Ile Lys Cys Asp Tyr Leu Ser Pro Ile Gly Phe Asp Tyr Leu Glu Asn
        195                 200                 205

Gly Ile Pro Val Thr Met Val Asn Trp Val Asp Lys Asp Gly Asn Asp
        210                 215                 220

Leu Pro Asp Gly Ala Asp Gln Asp Leu Lys Ala Gly Met Tyr Phe Ser
225                 230                 235                 240

Phe Ser Ser Asp Glu Thr Asn Ile Val Asp Thr Gly Asn Gly Tyr
            245                 250                 255

Tyr Gly Gly Tyr Tyr Trp Arg Leu Phe Glu Phe Gly Gln Phe Gly Pro
            260                 265                 270

Val Trp Leu Ser Cys Trp Asn Lys Asp Leu Val Asn Tyr Phe Gln
            275                 280                 285

```
<210> SEQ ID NO 4
<211> LENGTH: 495
<212> TYPE: PRT
<213> ORGANISM: Unknown
<220> FEATURE:
<221> NAME/KEY: source
<223> OTHER INFORMATION: /note="Description of Unknown:
      LysK lysin sequence"

<400> SEQUENCE: 4
```

Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly

```
                35                  40                  45
Tyr Tyr His Ala Gln Cys Gln Asp Leu Ile Thr Asp Tyr Val Leu Trp
 50                  55                  60
Leu Thr Asp Asn Lys Val Arg Thr Trp Gly Asn Ala Lys Asp Gln Ile
 65                  70                  75                  80
Lys Gln Ser Tyr Gly Thr Gly Phe Lys Ile His Glu Asn Lys Pro Ser
                 85                  90                  95
Thr Val Pro Lys Lys Gly Trp Ile Ala Val Phe Thr Ser Gly Ser Tyr
            100                 105                 110
Glu Gln Trp Gly His Ile Gly Ile Val Tyr Asp Gly Gly Asn Thr Ser
            115                 120                 125
Thr Phe Thr Ile Leu Glu Gln Asn Trp Asn Gly Tyr Ala Asn Lys Lys
130                 135                 140
Pro Thr Lys Arg Val Asp Asn Tyr Tyr Gly Leu Thr His Phe Ile Glu
145                 150                 155                 160
Ile Pro Val Lys Ala Gly Thr Thr Val Lys Lys Thr Ala Lys Lys
                165                 170                 175
Ser Ala Ser Lys Thr Pro Ala Pro Lys Lys Ala Thr Leu Lys Val
            180                 185                 190
Ser Lys Asn His Ile Asn Tyr Thr Met Asp Lys Arg Gly Lys Lys Pro
            195                 200                 205
Glu Gly Met Val Ile His Asn Asp Ala Gly Arg Ser Ser Gly Gln Gln
210                 215                 220
Tyr Glu Asn Ser Leu Ala Asn Ala Gly Tyr Ala Arg Tyr Ala Asn Gly
225                 230                 235                 240
Ile Ala His Tyr Tyr Gly Ser Glu Gly Tyr Val Trp Glu Ala Ile Asp
                245                 250                 255
Ala Lys Asn Gln Ile Ala Trp His Thr Gly Asp Gly Thr Gly Ala Asn
            260                 265                 270
Ser Gly Asn Phe Arg Phe Ala Gly Ile Glu Val Cys Gln Ser Met Ser
            275                 280                 285
Ala Ser Asp Ala Gln Phe Leu Lys Asn Glu Gln Ala Val Phe Gln Phe
290                 295                 300
Thr Ala Glu Lys Phe Lys Glu Trp Gly Leu Thr Pro Asn Arg Lys Thr
305                 310                 315                 320
Val Arg Leu His Met Glu Phe Val Pro Thr Ala Cys Pro His Arg Ser
                325                 330                 335
Met Val Leu His Thr Gly Phe Asn Pro Val Thr Gln Gly Arg Pro Ser
            340                 345                 350
Gln Ala Ile Met Asn Lys Leu Lys Asp Tyr Phe Ile Lys Gln Ile Lys
            355                 360                 365
Asn Tyr Met Asp Lys Gly Thr Ser Ser Ser Thr Val Val Lys Asp Gly
            370                 375                 380
Lys Thr Ser Ser Ala Ser Thr Pro Ala Thr Arg Pro Val Thr Gly Ser
385                 390                 395                 400
Trp Lys Lys Asn Gln Tyr Gly Thr Trp Tyr Lys Pro Glu Asn Ala Thr
                405                 410                 415
Phe Val Asn Gly Asn Gln Pro Ile Val Thr Arg Ile Gly Ser Pro Phe
            420                 425                 430
Leu Asn Ala Pro Val Gly Gly Asn Leu Pro Ala Gly Ala Thr Ile Val
            435                 440                 445
Tyr Asp Glu Val Cys Ile Gln Ala Gly His Ile Trp Ile Gly Tyr Asn
450                 455                 460
```

```
Ala Tyr Asn Gly Asn Arg Val Tyr Cys Pro Val Arg Thr Cys Gln Gly
465                 470                 475                 480

Val Pro Pro Asn Gln Ile Pro Gly Val Ala Trp Gly Val Phe Lys
            485                 490                 495

<210> SEQ ID NO 5
<211> LENGTH: 339
<212> TYPE: PRT
<213> ORGANISM: Unknown
<220> FEATURE:
<221> NAME/KEY: source
<223> OTHER INFORMATION: /note="Description of Unknown:
      Cpl-1 lysin sequence"

<400> SEQUENCE: 5

Met Val Lys Lys Asn Asp Leu Phe Val Asp Val Ser His Asn Gly
1               5                   10                  15

Tyr Asp Ile Thr Gly Ile Leu Glu Gln Met Gly Thr Thr Asn Thr Ile
                20                  25                  30

Ile Lys Ile Ser Glu Ser Thr Thr Tyr Leu Asn Pro Cys Leu Ser Ala
            35                  40                  45

Gln Val Glu Gln Ser Asn Pro Ile Gly Phe Tyr His Phe Ala Arg Phe
50                  55                  60

Gly Gly Asp Val Ala Glu Ala Glu Arg Glu Ala Gln Phe Phe Leu Asp
65                  70                  75                  80

Asn Val Pro Met Gln Val Lys Tyr Leu Val Leu Asp Tyr Glu Asp Asp
                85                  90                  95

Pro Ser Gly Asp Ala Gln Ala Asn Thr Asn Ala Cys Leu Arg Phe Met
            100                 105                 110

Gln Met Ile Ala Asp Ala Gly Tyr Lys Pro Ile Tyr Tyr Ser Tyr Lys
            115                 120                 125

Pro Phe Thr His Asp Asn Val Asp Tyr Gln Gln Ile Leu Ala Gln Phe
130                 135                 140

Pro Asn Ser Leu Trp Ile Ala Gly Tyr Gly Leu Asn Asp Gly Thr Ala
145                 150                 155                 160

Asn Phe Glu Tyr Phe Pro Ser Met Asp Gly Ile Arg Trp Trp Gln Tyr
                165                 170                 175

Ser Ser Asn Pro Phe Asp Lys Asn Ile Val Leu Leu Asp Asp Glu Glu
            180                 185                 190

Asp Asp Lys Pro Lys Thr Ala Gly Thr Trp Lys Gln Asp Ser Lys Gly
            195                 200                 205

Trp Trp Phe Arg Arg Asn Asn Gly Ser Phe Pro Tyr Asn Lys Trp Glu
210                 215                 220

Lys Ile Gly Gly Val Trp Tyr Tyr Phe Asp Ser Lys Gly Tyr Cys Leu
225                 230                 235                 240

Thr Ser Glu Trp Leu Lys Asp Asn Glu Lys Trp Tyr Tyr Leu Lys Asp
                245                 250                 255

Asn Gly Ala Met Ala Thr Gly Trp Val Leu Val Gly Ser Glu Trp Tyr
            260                 265                 270

Tyr Met Asp Asp Ser Gly Ala Met Val Thr Gly Trp Val Lys Tyr Lys
            275                 280                 285

Asn Asn Trp Tyr Tyr Met Thr Asn Glu Arg Gly Asn Met Val Ser Asn
            290                 295                 300

Glu Phe Ile Lys Ser Gly Lys Gly Trp Tyr Phe Met Asn Thr Asn Gly
305                 310                 315                 320
```

-continued

```
Glu Leu Ala Asp Asn Pro Ser Phe Thr Lys Glu Pro Asp Gly Leu Ile
                325                 330                 335

Thr Val Ala

<210> SEQ ID NO 6
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Met Thr Tyr Thr Leu Ser Lys Arg Ser Leu Asp Asn Leu Lys Gly Val
1               5                   10                  15

His Pro Asp Leu Val Ala Val His Arg Ala Ile Gln Leu Thr Pro
            20                  25                  30

Val Asp Phe Ala Val Ile Glu Gly Leu Arg Ser Val Ser Arg Gln Lys
            35                  40                  45

Glu Leu Val Ala Ala Gly Ala Ser Lys Thr Met Asn Ser Arg His Leu
        50                  55                  60

Thr Gly His Ala Val Asp Leu Ala Ala Tyr Val Asn Gly Ile Arg Trp
65                  70                  75                  80

Asp Trp Pro Leu Tyr Asp Ala Ile Ala Val Ala Val Lys Ala Ala Ala
                85                  90                  95

Lys Glu Leu Gly Val Ala Ile Val Trp Gly Gly Asp Trp Thr Thr Phe
            100                 105                 110

Lys Asp Gly Pro His Phe Glu Leu Asp Arg Ser Lys Tyr Arg
            115                 120                 125

<210> SEQ ID NO 7
<211> LENGTH: 147
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Met Lys Ile Ser Leu Glu Gly Leu Ser Leu Ile Lys Lys Phe Glu Gly
1               5                   10                  15

Cys Lys Leu Glu Ala Tyr Lys Cys Ser Ala Gly Val Trp Thr Ile Gly
            20                  25                  30

Tyr Gly His Thr Ala Gly Val Lys Glu Gly Asp Val Cys Thr Gln Glu
            35                  40                  45

Glu Ala Glu Lys Leu Leu Arg Gly Asp Ile Phe Lys Phe Glu Glu Tyr
        50                  55                  60

Val Gln Asp Ser Val Lys Val Asp Leu Asp Gln Ser Gln Phe Asp Ala
65                  70                  75                  80

Leu Val Ala Trp Thr Phe Asn Leu Gly Pro Gly Asn Leu Arg Ser Ser
                85                  90                  95

Thr Met Leu Lys Lys Leu Asn Asn Gly Glu Tyr Glu Ser Val Pro Phe
            100                 105                 110

Glu Met Arg Arg Trp Asn Lys Ala Gly Gly Lys Thr Leu Asp Gly Leu
            115                 120                 125

Ile Arg Arg Arg Gln Ala Glu Ser Leu Leu Phe Glu Ser Lys Glu Trp
        130                 135                 140
```

His Gln Val
145

<210> SEQ ID NO 8
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Met Arg Thr Ser Gln Arg Gly Ile Asp Leu Ile Lys Ser Phe Glu Gly
1               5                   10                  15

Leu Arg Leu Ser Ala Tyr Gln Asp Ser Val Gly Val Trp Thr Ile Gly
            20                  25                  30

Tyr Gly Thr Thr Arg Gly Val Thr Arg Tyr Met Thr Ile Thr Val Glu
        35                  40                  45

Gln Ala Glu Arg Met Leu Ser Asn Asp Ile Gln Arg Phe Glu Pro Glu
    50                  55                  60

Leu Asp Arg Leu Ala Lys Val Pro Leu Asn Gln Asn Gln Trp Asp Ala
65                  70                  75                  80

Leu Met Ser Phe Val Tyr Asn Leu Gly Ala Ala Asn Leu Ala Ser Ser
                85                  90                  95

Thr Leu Leu Lys Leu Leu Asn Lys Gly Asp Tyr Gln Gly Ala Ala Asp
            100                 105                 110

Gln Phe Pro Arg Trp Val Asn Ala Gly Gly Lys Arg Leu Asp Gly Leu
        115                 120                 125

Val Lys Arg Arg Ala Ala Glu Arg Ala Leu Phe Leu Glu Pro Leu Ser
    130                 135                 140

<210> SEQ ID NO 9
<211> LENGTH: 181
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Met Asn Asn Glu Leu Pro Trp Val Ala Glu Ala Arg Lys Tyr Ile Gly
1               5                   10                  15

Leu Arg Glu Asp Thr Ser Lys Thr Ser His Asn Pro Lys Leu Leu Ala
            20                  25                  30

Met Leu Asp Arg Met Gly Glu Phe Ser Asn Glu Ser Arg Ala Trp Trp
        35                  40                  45

His Asp Asp Glu Thr Pro Trp Cys Gly Leu Phe Val Gly Tyr Cys Leu
    50                  55                  60

Gly Val Ala Gly Arg Tyr Val Val Arg Glu Trp Tyr Arg Ala Arg Ala
65                  70                  75                  80

Trp Glu Ala Pro Gln Leu Thr Lys Leu Asp Arg Pro Ala Tyr Gly Ala
                85                  90                  95

Leu Val Thr Phe Thr Arg Ser Gly Gly Gly His Val Gly Phe Ile Val
            100                 105                 110

Gly Lys Asp Ala Arg Gly Asn Leu Met Val Leu Gly Gly Asn Gln Ser
        115                 120                 125

```
Asn Ala Val Ser Ile Ala Pro Phe Ala Val Ser Arg Val Thr Gly Tyr
            130                 135                 140

Phe Trp Pro Ser Phe Trp Arg Asn Lys Thr Ala Val Lys Ser Val Pro
145                 150                 155                 160

Phe Glu Glu Arg Tyr Ser Leu Pro Leu Leu Lys Ser Asn Gly Glu Leu
                165                 170                 175

Ser Thr Asn Glu Ala
            180
```

<210> SEQ ID NO 10
<211> LENGTH: 439
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

```
Met Lys Arg Thr Thr Leu Asn Leu Glu Leu Glu Ser Asn Thr Asp Arg
1               5                   10                  15

Leu Leu Gln Glu Lys Asp Asp Leu Leu Pro Gln Ser Val Thr Asn Ser
            20                  25                  30

Ser Asp Glu Gly Thr Pro Phe Ala Gln Val Glu Gly Ala Ser Asp Asp
        35                  40                  45

Asn Thr Ala Glu Gln Asp Ser Asp Lys Pro Gly Ala Ser Val Ala Asp
    50                  55                  60

Ala Asp Thr Lys Pro Val Asp Pro Glu Trp Lys Thr Ile Thr Val Ala
65                  70                  75                  80

Ser Gly Asp Thr Leu Ser Thr Val Phe Thr Lys Ala Gly Leu Ser Thr
                85                  90                  95

Ser Ala Met His Asp Met Leu Thr Ser Ser Lys Asp Ala Lys Arg Phe
            100                 105                 110

Thr His Leu Lys Val Gly Gln Glu Val Lys Leu Lys Leu Asp Pro Lys
        115                 120                 125

Gly Glu Leu Gln Ala Leu Arg Val Lys Gln Ser Glu Leu Glu Thr Ile
    130                 135                 140

Gly Leu Asp Lys Thr Asp Lys Gly Tyr Ser Phe Lys Arg Glu Lys Ala
145                 150                 155                 160

Gln Ile Asp Leu His Thr Ala Tyr Ala His Gly Arg Ile Thr Ser Ser
                165                 170                 175

Leu Phe Val Ala Gly Arg Asn Ala Gly Leu Pro Tyr Asn Leu Val Thr
            180                 185                 190

Ser Leu Ser Asn Ile Phe Gly Tyr Asp Ile Asp Phe Ala Leu Asp Leu
        195                 200                 205

Arg Glu Gly Asp Glu Phe Asp Val Ile Tyr Glu Gln His Lys Val Asn
    210                 215                 220

Gly Lys Gln Val Ala Thr Gly Asn Ile Leu Ala Ala Arg Phe Val Asn
225                 230                 235                 240

Arg Gly Lys Thr Tyr Thr Ala Val Arg Tyr Thr Asn Lys Gln Gly Asn
                245                 250                 255

Thr Ser Tyr Tyr Arg Ala Asp Gly Ser Ser Met Arg Lys Ala Phe Ile
            260                 265                 270

Arg Thr Pro Val Asp Phe Ala Arg Ile Ser Ser Arg Phe Ser Leu Gly
        275                 280                 285

Arg Arg His Pro Ile Leu Asn Lys Ile Arg Ala His Lys Gly Val Asp
```

```
                    290                 295                 300

Tyr Ala Ala Pro Ile Gly Thr Pro Ile Lys Ala Thr Gly Asp Gly Lys
305                 310                 315                 320

Ile Leu Glu Ala Gly Arg Lys Gly Tyr Gly Asn Ala Val Val Ile
                325                 330                 335

Gln His Gly Gln Arg Tyr Arg Thr Ile Tyr Gly His Met Ser Arg Phe
                340                 345                 350

Ala Lys Gly Ile Arg Ala Gly Thr Ser Val Lys Gln Gly Gln Ile Ile
                355                 360                 365

Gly Tyr Val Gly Met Thr Gly Leu Ala Thr Gly Pro His Leu His Tyr
                370                 375                 380

Glu Phe Gln Ile Asn Gly Arg His Val Asp Pro Leu Ser Ala Lys Leu
385                 390                 395                 400

Pro Met Ala Asp Pro Leu Gly Gly Ala Asp Arg Lys Arg Phe Met Ala
                405                 410                 415

Gln Thr Gln Pro Met Ile Ala Arg Met Asp Gln Glu Lys Lys Thr Leu
                420                 425                 430

Leu Ala Leu Asn Lys Gln Arg
                435

<210> SEQ ID NO 11
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asn Lys Gly Asp Tyr Gln Gly Ala Ala Asp Gln Phe Pro Arg Trp Val
1               5                   10                  15

Asn Ala Gly Gly Lys Arg Leu Asp Gly Leu Val Lys Arg Arg Ala Ser
                20                  25                  30

Gln Ser Arg Glu Ser Gln Cys
        35

<210> SEQ ID NO 12
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asn Lys Gly Asp Tyr Gln Gly Ala Ala Asp Gln Phe Pro Arg Trp Val
1               5                   10                  15

Asn Ala Gly Gly Lys Arg Leu Asp Gly Leu Val Lys Arg Arg Ala Ala
                20                  25                  30

Glu Arg Ala Leu Phe Leu Glu Pro Leu Ser
        35                  40

<210> SEQ ID NO 13
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic polypeptide"

<400> SEQUENCE: 13

Asn Lys Gly Asp Tyr Gln Gly Ala Ala Asp Gln Phe Pro Arg Trp Val
1               5                   10                  15

Asn Ala Gly Gly Lys Arg Leu Asp Gly Leu Val Lys Arg Arg Ala
            20                  25                  30

<210> SEQ ID NO 14
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Asn Lys Gly Asp Tyr Gln Gly Ala Ala Asp Gln Phe Pro Arg Trp Val
1               5                   10                  15

Asn Ala Gly Gly Lys Arg Leu Asp Gly Leu Val Lys Arg Arg Lys
            20                  25                  30

<210> SEQ ID NO 15
<211> LENGTH: 43
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asn Lys Gly Asp Tyr Gln Gly Ala Ala Asp Gln Phe Pro Arg Trp Val
1               5                   10                  15

Asn Ala Gly Gly Lys Arg Leu Asp Gly Leu Val Lys Arg Arg Ala Ala
            20                  25                  30

Glu Arg Ala Leu Phe Leu Glu Pro Leu Ser Cys
            35                  40

<210> SEQ ID NO 16
<211> LENGTH: 495
<212> TYPE: PRT
<213> ORGANISM: Unknown
<220> FEATURE:
<223> OTHER INFORMATION: Description of Unknown:
      PAL lysin peptide

<400> SEQUENCE: 16

Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly
            35                  40                  45

Tyr Tyr His Ala Gln Cys Gln Asp Leu Ile Thr Asp Tyr Val Leu Trp
        50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr

```
              100                 105                 110
Glu Gln Trp Gly His Ile Gly Ile Val Tyr Asp Gly Gly Asn Thr Ser
            115                 120                 125

Thr Phe Thr Ile Leu Glu Gln Asn Trp Asn Gly Tyr Ala Asn Lys Lys
130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Ala Thr Leu Lys Val
            180                 185                 190

Ser Lys Asn His Ile Asn Tyr Thr Met Asp Lys Arg Gly Lys Lys Pro
            195                 200                 205

Glu Gly Met Val Ile His Asn Asp Ala Gly Arg Ser Ser Gly Gln Gln
            210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
            275                 280                 285

Ala Ser Asp Ala Gln Phe Leu Lys Asn Glu Gln Ala Val Phe Gln Phe
            290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
            355                 360                 365

Asn Tyr Met Asp Lys Gly Thr Ser Ser Ser Thr Val Val Lys Asp Gly
            370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
                405                 410                 415

Phe Val Asn Gly Asn Gln Pro Ile Val Thr Arg Ile Gly Ser Pro Phe
            420                 425                 430

Leu Asn Ala Pro Val Gly Gly Asn Leu Pro Ala Gly Ala Thr Ile Val
            435                 440                 445

Tyr Asp Glu Val Cys Ile Gln Ala Gly His Ile Trp Ile Gly Tyr Asn
450                 455                 460

Ala Tyr Asn Gly Asn Arg Val Tyr Cys Pro Val Arg Thr Cys Gln Gly
465                 470                 475                 480

Val Pro Pro Asn Gln Ile Pro Gly Val Ala Trp Gly Val Phe Lys
            485                 490                 495
```